United States Patent [19]

Mehra

[11] Patent Number: 4,743,282
[45] Date of Patent: May 10, 1988

[54] SELECTIVE PROCESSING OF GASES CONTAINING OLEFINS BY THE MEHRA PROCESS

[75] Inventor: Yuv R. Mehra, Odessa, Tex.

[73] Assignee: Advanced Extraction Technologies, Inc., Houston, Tex.

[21] Appl. No.: 854,383

[22] Filed: Apr. 21, 1986

Related U.S. Application Data

[63] Continuation-in-part of Ser. No. 828,996, Feb. 13, 1986, Pat. No. 4,696,688, and Ser. No. 828,988, Feb. 13, 1986, Pat. No. 4,680,042, each is a continuation-in-part of Ser. No. 808,463, Dec. 13, 1985, Pat. No. 4,692,179, which is a continuation-in-part of Ser. No. 784,566, Oct. 4, 1985, Pat. No. 4,617,038, which is a continuation-in-part of Ser. No. 759,327, Jul. 26, 1985, Pat. No. 4,623,371, which is a continuation-in-part of Ser. No. 758,351, Jul. 24, 1985, Pat. No. 4,601,738, which is a continuation-in-part of Ser. No. 637,210, Aug. 3, 1984, Pat. No. 4,578,094, which is a continuation-in-part of Ser. No. 532,005, Sep. 14, 1983, Pat. No. 4,526,594, which is a continuation-in-part of Ser. No. 507,564, Jun. 24, 1983, Pat. No. 4,511,381, which is a continuation-in-part of Ser. No. 374,270, May 3, 1982, Pat. No. 4,421,535.

[51] Int. Cl.$^4$ ............................................... F25J 3/00
[52] U.S. Cl. ............................................. 62/17; 55/68; 55/76; 62/20
[58] Field of Search ................. 62/17, 20; 55/68, 76

[56] References Cited

U.S. PATENT DOCUMENTS

| | | | |
|---|---|---|---|
| 1,875,311 | 8/1932 | Voorhees et al. | 55/23 |
| 2,187,631 | 1/1940 | Schutt | 196/9 |
| 2,282,549 | 5/1941 | Sullivan Jr., et al. | 196/9 |
| 2,308,856 | 1/1943 | Borden | 196/10 |
| 2,325,379 | 7/1943 | Durrum | 202/40 |
| 2,357,028 | 8/1944 | Shiras et al. | 202/67 |
| 2,392,739 | 1/1946 | Horeczy et al. | 260/677 |
| 2,433,286 | 12/1947 | McKinnis | 202/39.5 |
| 2,455,803 | 12/1948 | Pierotti | 202/39.5 |
| 2,511,206 | 6/1950 | Hasche | 260/679 |
| 2,516,507 | 7/1950 | Deming | 183/115 |
| 2,570,066 | 10/1951 | Morrow et al. | 202/39.5 |
| 2,573,341 | 10/1951 | Kniel | 260/683 |
| 2,588,323 | 3/1952 | Kniel | 260/677 |
| 2,780,580 | 2/1957 | Kniel | 196/8 |
| 2,804,488 | 8/1957 | Cobb | 260/683 |
| 2,814,359 | 11/1957 | Koble | 183/115 |
| 2,846,443 | 8/1953 | Malusa et al. | 260/326.5 |
| 2,849,371 | 8/1958 | Gilmore | 196/8 |
| 3,055,183 | 9/1962 | Kniel | 62/17 |
| 3,082,271 | 3/1963 | Weitz et al. | 260/677 |
| 3,349,145 | 10/1967 | Uitti | 260/672 |
| 3,686,344 | 8/1972 | Brunner et al. | 260/679 |
| 4,072,604 | 2/1978 | Ward | 208/101 |
| 4,479,812 | 10/1984 | Hsia et al. | 55/50 |

FOREIGN PATENT DOCUMENTS 2142041A 1/1985 United Kingdom ................. 7/11

OTHER PUBLICATIONS

"International Search Report" from the European Patent Office as the International Searching Authority for the corresponding PCT Application Serial No. 86/01,674, filed Aug. 15, 1986 in the RO/US.

"Low Temperature Processing of Light Hydrocarbons", by A. W. Pratt and N. L. Foskett, *Transactions of the American Institute of Chemical Engineers*, vol. 42, 1946, pp. 149–163.

(Continued on next page.)

*Primary Examiner*—Ronald C. Capossela
*Attorney, Agent, or Firm*—Depaoli & O'Brien

[57] ABSTRACT

A gas-liquid extractive stripping process is disclosed which uses at least one preferential physical solvent in at least one solvent loop, each loop passing through at least two unit operations: extractive-stripping and distillation. At least the first extractive-stripping operation may additionally comprise a rectification section on top of the extraction section. Three products are made from streams of thermally cracked gases or refinery gases: a hydrogen-rich gas stream, a methane-rich gas stream, and a $C_2=+$ hydrocarbons stream which is the feed stream for the conventional fractionation train of an olefins manufacturing facility. Ethylene can be economically produced from the $C_2=+$ hydrocarbons product stream at a recovery of at least 99.5% and a purity of at least 99.9%.

57 Claims, 5 Drawing Sheets

OTHER PUBLICATIONS

"Production of Ethylene from Ethane, Propane", by H. C. Schutt, *Chemical Engineering Progress*, vol. 43, No. 3, Mar. 1947, pp. 103–116.

"Ethylene Purification by Absorption Process", by Ludwig Kniel and W. H. Slager, *Chemical Engineering Progress*, Jul. 1947, vol. 43, No. 7, pp. 335–342.

"Propane Recovery by Absorption", by Ludwig Kniel, *Petroleum Refiner*, vol. 27, No. 11, Nov. 1948, pp. 108–113.

*Petroleum Refinery Engineering*, by W. L. Nelson, Third Edition, McGraw-Hill Book Company, Inc., New York, N.Y., 1949 pp. 651–652 and 729–745.

"Humble's Avery Island Plant: High Safety at Low Cost", by Joe J. Weatherby, *Hydrocarbon Processing & Petroleum Refiner*, Apr. 1962, vol. 41, No. 4.

"Ethylene Recovery, Pyrolysis-Product Pretreatment", by S. B. Zdonik, E. D. Green, and L. P. Hallee, *Oil & Gas Journal*, Petroleum Publishing Co., 1970, pp. 85–86.

"Ethylene-Keystone to the Petrochemical Industry", L. Kniel, O. Winter, and K. Stork, Marcel Dekker, Inc., New York, N.Y., 1980, pp. 72–73, 78–94, 143–145, and 158–172.

"Ethylene from NGL feedstocks", Part 3—Flow scheme comparison, L. K. Mg, C. N. Eng., and R. S. Zack, *Hydrocarbon Processing*, Dec. 1983, pp. 99–102.

"The Purification of Ethylene", pp. 129–133 of The Recovery of Ethylene in a Modern Plant, vol. 20 of *Encyclopedia of Chemical Processing and Design*, edited by John J. McKetta and William A. Cunningham, Marcel Dekker, Inc., New York, N.Y., Aug. 1984.

"New Capacity Forces Ethylene Producers to Aim for Lower Costs, Flexibility", by Ted Wett, *Oil and Gas Journal*, Sep. 2, 1985, pp. 39–44.

*Gas Processors Report, Texas Coast*, Spears Consulting Group, P.O. Box 33002, Tulsa, OK 74153, Oct. 14, 1985, pp. 1–8.

"The Talk of Europe: Mossmorran's New Cracker", by Herb Short, *Chemical Engineering*, Jan. 20, 1986, pp. 31–32.

TYPICAL OLEFINS FACILITY

SIMPLIFIED OLEFINS SEPARATION

SELECTIVE PROCESSING OF GASES CONTAINING OLEFINS BY THE MEHRA PROCESS

RELATED APPLICATIONS

This is a continuation-in-part of co-pending application Ser. No. 828,996, filed Feb. 13, 1986 now U.S. Pat. No. 4,696,688, and of co-pending application Ser. No. 828,988, filed Feb. 13, 1986 now U.S. Pat. No. 4,680,042, which are continuations-in-part of co-pending application Ser. No. 808,463, filed Dec. 13, 1985 now U.S. Pat. No. 4,696,179, which is a continuation-in-part of co-pending application Ser. No. 784,566, filed Oct. 4, 1985, now U.S. Pat. No. 4,617,038 which is a continuation-in-part of co-pending application Ser. No. 759,327, filed July 26, 1985, now U.S. Pat. No. 4,623,371 which is a continuation-in-part of co-pending application Ser. No. 758,351, filed July 24, 1985, now U.S. Pat. No. 4,601,738, which is a continuation-in-part of co-pending application Ser. No. 637,210, filed Aug. 3, 1984, now U.S. Pat. No. 4,478,094,which is a continuation-in-part of application Ser. No. 532,005, filed Sept. 14, 1983, now U.S. Pat. No. 4,526,594, which is a continuation-in-part of application Ser. No. 507,564, filed June 24, 1983, now U.S. Pat. No. 4,511,381, which is a continuation-in-part of application Ser. No. 374,270, filed May 3, 1982, now U.S. Pat. No. 4,421,535.

BACKGROUND OF THE INVENTION

1. Field of the Invention

This invention relates to recovery of olefins from pryolyzed hydrocarbon gases and especially relates to recovery of olefins from cracked hydrocarbon gases by absorption with a preferential physical solvent.

2. Review of the Prior Art

Olefins have a wide variety of petrochemical uses. Ethylene is a principal building block of the petrochemical industry. Its largest single use is the conversion to low-and high-density polyethylenes, which are used in packaging, communications, construction, automotive, manufacturing of home appliances, and many other industries. Other major uses include oxidation to ethylene oxide and chlorination to ethylene dichloride.

Olefins are generally produced by thermally or catalytically cracking gaseous or liquid hydrocarbons to make cracked gases. Three general methods of separating or concentrating the components of cracked gases for the recovery of ethylene of moderate and high purity have been available for many years. One involves use of a solid adsorbent such as charcoal or silica gel. The other two utilize fractional distillation in two variations, the first being a straight low-temperature fractionation process and the second involving absorption into liquid having low vapor pressure, thereby avoiding very low temperatures in the fractionation system.

Low-temperature fractionation, a refinement of the stepwise liquefaction method, was used as of about the mid-1960's in the majority of ethylene plants in operation, as described in "Low Temperature Fractionation of Light Hydrocarbons", by A. W. Pratt and N. L. Foskett, Transactions of the American Institute of Chemical Engineers, Vol. 42, 1946, page 149.

In a typical modern olefin plant employing low-temperature fractionation for ethylene recovery as illustrated in FIG. 1, the predominant feedstock is composed of ethane, propane, butanes, naphtha, gas oil, condensate, and other hydrocarbons derived from petroleum cracking. These feedstocks are pretreated and cracked by conventional steam crackers. The cracked gases leave the cracking furnaces at 1500° to 2200° F. These gases are quenched and cooled down to about 80° to 120° F. at pressures less than 15 psig. The above feedstocks may also be catalytically cracked under appropriate operating conditions.

Depending upon the feedstock and the severity and selectivity of cracking, the cracked gases comprise hydrogen, methane, carbon monoxide, carbon dioxide, acetylene, ethylene, ethane, methyl acetylene, propadiene, propylene, propane, butadienes, butenes, butanes, $C_5$'s, $C_6$-$C_8$ non-aromatics, benzene, toluene, xylene, ethyl benzene, styrene, $C_9$-400° F. gasoline, 400+° F. fuel oil and water.

These gases are compressed in multi-stage compression units to pressures in the order of 400 to 600 psig. During compression, some heavier hydrocarbons and water are separated. Depending upon their composition, the separated hydrocarbons are stabilized and may be utilized as part of the feed to the fractionation train. The uncondensed gases after compression are further dried by molecular sieves or activated alumina to a water dew point of less than −150° F. The cracked gases may be dried at an intermediate pressure level consistent with the interstage pressure of the multi-stage cracked gas compressor.

The dry gases are then chilled in a series of steps to cryogenic temperatures of −200° F. through a complicated set of equipment utilizing extensive heat exchange and ethylene and propylene refrigeration systems. The purpose of chill-down is to separate ethylene and heavier hydrocarbons from the methane and hydrogen present in the cracked gases. The remaining stream of methane and hydrogen is further separated into hydrogen-rich and methane-rich streams within the cryogenic chill-down train. A part of the separated hydrogen stream is preferably further purified by using conventional pressure swing adsorption techniques before utilizing it for hydrogenating acetylenes to desirable products while the methane-rich stream is used as fuel gas for the steam cracking furnaces.

The separated liquid streams, containing ethylene and heavier hydrocarbons, are further fractionated in a low-to-high-pressure demethanizer (150 to 450 psig). The low-pressure demethanizer utilizes ethylene refrigerant for the overhead condenser while the high-pressure demethanizer uses low-level propylene refrigerant, sometimes in conjunction with an expander unit, for such condensation.

The specification of methane in the bottom of the demethanizer is quite stringent since methane represents an impurity when present with the ethylene product. Similarly, it is highly desirable to recover most of the ethylene present in feeds to the demethanizer in order to reduce its loss and thus minimize the need for recycling demethanizer overhead to the cracked gas compressors for additional recovery of this desirable product.

The olefin plants are known to be energy intensive. For a 1.4 billion pounds per year ethylene-capacity plant using modern available technology for 50/50 condensate and ethane/propane feedstock, the charge gas compressor requirements can vary between 36,000 and 39,000 horsepower (HP) while the corresponding requirements for the propylene refrigeration system can vary from 18,000 to 22,000 HP and those for the ethylene refrigeration system can vary from 3,900 to 8,000

HP. Thus, depending upon the technology involved and the desired product slate, the total compression energy can vary between 58,700 and 69,000 HP, thereby requiring large capital investment and representing a significant cost of operation related to energy consumption. In summary, depending upon the desired product slate, available feedstock, severity, and selectivity of cracking and separations technology utilized, the specific energy consumption of an olefins plant can vary between 5,500 and 13,500 Btu/Lb of ethylene product. This represents about 25.4% to 62.4% of the gross heating value of ethylene of 21,629 Btu/Lb.

It is important to note that the cracking system for olefin production appears to have been improved and refined to an operating state of high efficiency. Even though the steam crackers require significant amounts of fuel, since the cracking process occurs at extremely high temperatures, most of the energy expended in the cracking furnaces is recovered through extensive use of waste heat recovery equipment. For example, of the energy which is liberated by thermally cracking the hot gases, only about 3–5% is lost, and that loss is through the stacks. Most of the energy thus recovered is utilized for compressing the cracked gases and providing refrigeration for the chill-down train. Therefore, the major energy consumption in an olefins facility is associated with the chill-down and fractionation train in order to separate various components of the cracked gas stream.

According to a recent article, there are twenty-three companies that operate thirty-two olefin plants in the United States of America. This article is entitled, "New Capacity Forces Ethylene Producers to Aim for Lower Costs, Flexibility", by Ted Wett, and appeared in the Sept. 2, 1985 issue of *Oil and Gas Journal*, page 39. The equivalent total installed production capacity of these thirty-two plants or facilities was about 38 billion pounds per year of ethylene as of June 1985. On a worldwide basis, the total ethylene plant capacity was about 108 billion pounds per year as of about June 1985. The feedstocks used for plants or facilities was at least one of ethane, propane, butane, refinery streams, naphtha, gas oil, natural gas liquids (NGL), liquefied petroleum gas (LPG), etc.

As an example of the most modern ethylene facilities, Europe's newest ethylene crackers started production in about October 1985 in a $1.6 billion plant at Mossmoran, Scotland with six cracking furnaces operating on ethane as feedstock. It is the first cracking facility known to use a gas turbine to drive the process-gas compressor and the first to employ the turbine exhaust gas as preheat combustion air for the furnaces. As the other side of the ethylene capacity coin, about 600,000 metric tons per year of cracking facilities are being shut down in England and Germany because of its competitive effects.

Problems with imbalance of capacity and demand have been plaguing the olefin production industry for many years. Nevertheless, new plants of steadily increasing size and complexity have been built that incorporate the newest technologies. In some instances, these plants exist for nationalistic reasons, whether or not they are profitable. In most cases, however, the plants come into existence because of cheap feedstock sources or because incorporating the newest technologies can enable a plant to compete successfully with older plants and capture a share of the existing market and/or of its anticipated expansion. As the newer plants come on-stream, the older plants may have to be shut down, reduced in capacity, or reduced in production costs.

Among the changes that can be instituted to effect cost reduction are changing the crackers to provide flexibility for processing a wide variety of feedstocks according to market conditions. Another cost-reducing step is to revise existing facilities in order to optimize feed and energy requirements, possibly including co-generation systems with various units. A third step is to make full use of computer control in order to maximize plant operating efficiency. A fourth step is to replace obsolete plants within a facility with more efficient plants using improved technology.

The next stage for improving efficiency of olefin production is believed to be replacement of low temperature plants for recovery and separation of olefins from cracked gases. Although the industry has docilely continued to utilize low-temperature fractionation for many years after discarding solvent absorption systems such as the Kniel process, it pays a relatively high price therefor because low-temperature fractionation requires extreme dehydration and achieves it by using energy-intensive ethylene and propylene refrigerating systems.

As of about 1948, according to page 651 of "Petroleum Refinery Engineering" by W. L. Nelson, third edition, McGraw-Hill Book Company, Inc., New York, N.Y., 1949, 830 pages, ethylene was fundamentally important in making many chemicals such as alcohol, ethylether, styrene, ethylene glycol, and tetraethyl lead. A total daily plant capacity of 3,370,000 lbs per day was being built or was in operation in 1948, not including plants producing ethylene for hydration to alcohol. The plants were mainly of the thermal decomposition type, operating primarily on ethane and propane, in which the cracked gases were fed to an absorber-stripper column producing fuel gas as overhead and a rich solvent which was fed to a de-ethanizer column as the first component of a fractionation train, as shown in FIG. 1 of U.S. Pat. No. 2,573,341 which is FIG. 2 of the drawings of this invention, as representative absorption prior art.

The absorption method is discussed for an absorption-type recovery plant in an article in Chemical Engineering Progress, by Ludwig Kniel and W. H. Slager, Vol. 43, No. 7, pages 335–342, July 1947, using the same process in its FIG. 2 that is illustrated on page 652 of the book, "Petroleum Refinery Engineering", and in FIG. 1 of U.S. Pat. No. 2,573,341.

This ethylene plant of Monsanto Chemical Co. at Texas City, Tex. was mainly used for producing ethylene and operated primarily on ethane and propane. Typical ultimate ethylene yields were 75 wt. % from ethane, 48 wt. % from propane, or 25–32 wt. % from gas oil. At a conversion per pass of about 45% when cracking propane, yields were about 16.7 wt. % of ethylene and 15.8 wt. % of propylene, once through. The ethylene was separated along with the ethane and heavier components by means of low-temperature absorption with an aromatic distillate produced in the process and containing more than 50% benzene and toluene by weight and appreciable quantities of naphthenes, among which cyclopentane and cyclohexane had been identified.

Typical analyses of three ethylene-bearing streams were given in this article: (a) a typical coke-oven gas, (b) a refinery off-gas, and (c) the effluent from a pyrolysis unit charging propane and operated to yield a maximum amount of ethylene. For these three stocks, ethylene concentration was 4–27 mol % and diluents lighter than ethylene were 94–17 mol %, thereby bracketing most commercial gases from which ethylene or ethylene+propylene might be economically recovered.

In an article in Petroleum Refiner, by Ludwig Kniel, Volume 27, No. 11, November 1948, the design of a fractionating absorber, which is essentially the same apparatus as the absorber-stripper discussed in the earlier article, is described for separating methane from ethylene in a pyrolysis gas obtained from the cracking of propane. It had been found in plant operations that the performance of such fractionating absorbers exceeded the requirements anticipated in the design as to both recovery and design purity. The reason therefor was speculated to be either due to the type of lean oil employed which contained substantial proportions of aromatics, particularly benzene, or the result of superimposed recirculation occurring between the plates where intercoolers were located.

An article in Hydrocarbon Processing & Petroleum Refiner, by Joe J. Weatherby, April 1962, Volume 41, No. 4, describes a low-temperature absorption plant which recovered 40% propane from 11 MMCFD of wet natural gas. This installation utilized a fractionator absorber having a reboiler and no intercoolers. This column not only absorbed the hydrocarbons from the gas stream but fractionated off the methane and ethane to yield a de-ethanized product. A portion of the $C_7+$ fraction of the product was pumped over the top of this column as absorption oil. Ethylene glycol was injected into the inlet gas stream upstream of the gas exchanger and of the inlet gas chiller wherein it was cooled to 20° F. with ammonia as refrigerant. A gas exchanger and inlet gas chiller removed about ½ of the heat of absorption outside of the absorber but they consequently lowered mean effective absorber temperature, and the oil content of the residue gas leaving the top of the column was in equilibrium with the oil at the minimum temperature of 20° F., thereby minimizing oil loss.

Numerous processes are known in the solvent absorption art for olefin recovery from cracked, refinery, and synthetic gases containing these unsaturated compounds. Some processes utilize an aromatic absorption oil as a solvent within an absorber-stripper column having a reboiler. Such processes are disclosed in one or more of U.S. Pat. Nos. 2,187,631, 2,282,549, 2,308,566, 2,325,379, 2,357,028, 2,433,286, 2,455,803, 2,570,066, 2,573,341, 2,588,323, 2,708,580, 2,849,371, 3,055,183, 3,082,271, 3,349,145, 3,686,344, 4,072,604, and 4,479,812.

U.S. Pat. No. 2,573,341 of Ludwig Kniel, which issued from Ser. No. 717,264, filed Dec. 7, 1946, relates to a process for recovering olefinic hydrocarbons and particularly high purity ethylene from coke oven gas, refinery off-gas, and pyrolysis gas, having respective ethylene contents of 4.0%, 5.0%, and 27.0 mol. %, which are the feedstocks to a rectifier-absorber, also known as an absorber-stripper. The column or tower has a reboiler at its bottom and two intercoolers to remove the heat of extraction. The overhead is fuel gas, and the bottoms are fed to a de-ethanizer column, having a reboiler at its bottom and a condenser for its overhead from which a portion of the condensate is returned to the de-ethanizer column as reflux. The lean oil rate is not over 4.2 lbs per lb of feed, an amount which assures the retention of 99 mol % of the ethylene entering the rectifier absorption tower.

Absorption, exemplified by the process in FIG. 1 of U.S. Pat. No. 2,573,341, was stated on page 651 of the Nelson book to be the process mainly used for ethylene recovery as of about 1948. In the mid-1950's, a number of absorption plants were in operation which utilized refrigerated lean oils such as propane, butane, or light aromatic fractions.

As of the mid-1960's, according to page 85 of "Manufacturing Ethylene", by S. B. Zdonik, E. D. Green, and L. P. Hallee, Petroleum Publishing Co., 1970, a few absorption plants were still in operation but were decreasing in number while all of the newly built plants employed some form of low-temperature fractionation to separate ethylene from light hydrocarbons At plant capacities of about 100 million lb/year of ethylene production, refrigerated-absorption recovery plants were economically comparable to low-temperature-fractionation recovery plants.

As the size of ethylene plants increased, the large heating and cooling loads imparted to the solvent in the absorption-type plants caused them to be more uneconomical from the standpoint of operating and plant costs, even though the low-temperature-fractionation plant used a more complicated refrigeration system because of the extreme low temperature involved.

Thus it appears that a classic competitive battle occurred during the twenty years from the end of World War II to about 1965, with the winner being declared the low-temperature fractionation plant and the loser being declared the solvent absorption plant. A review of the reasons for this decision of the marketplace is in order.

Referring to FIG. 1 of U.S. Pat. No. 2,573,341 as the dominant absorption process according to Nelson, there appear to be at least seven reasons that plants using the Kniel absorption process, for recovery and separation of olefins from thermally cracked hydrocarbon gases, failed to win the competitive battle. Firstly, it should be noted that this Kniel process was not applicable to the separation of methane from hydrogen, yet such separation was needed for hydrogenating acetylene to ethylene. Hydrogen was therefore used as fuel, an economically wasteful process.

Secondly, the process appears to have been biased toward the continuous production of aromatic fractions and retention thereof in the aromatic system to the extent necessary to maintain a supply of absorber oil. This situation indicates that the losses of lean absorption oil were considerable and that such losses went to fuel use. Indeed, the cracking furnaces appear to have been designed for producing the aromatic absorber oil rather than for producing ethylene.

Thirdly, it is stated in the '341 patent that it is also essential that methane be eliminated by the absorber-stripper column, without loss of ethylene in its overhead stream, and that larger amounts of methane than anticipated not be allowed in the bottoms material from the absorber-stripper column because such larger amounts could jeopardize the operation of the de-ethanizer and ethylene fractionator by causing an inability to condense the reflux in these towers at the temperatures required to obtain the desired concentrations in the overheads from each of these towers. According to an Amendment filed on Jan. 8, 1951 during the prosecution of Ser. No. 717,264, "It was found that in the design of such plant there was a tendency to either lose ethylene overhead in the fuel gas line or to accumulate methane in the bottoms of the absorber, which contaminated the ethylene product." The solution apparently adopted and claimed U.S. Pat. No. 2,573,341, as shown in its FIG. 2, was to add the demethanizer column, but the demethanizing column is superfluous if the absorber-stripper column is properly designed.

Fourthly, about 96% of the methane was rejected, thereby indicating that 4% of contained methane was present with the ethylene product, a figure that is substantiated by an ethylene purity of 97%. Purity requirements have steadily increased, however, and there may have been increased economic burdens for meeting these requirements that the Kniel-type absorption process was not able to meet.

Fifthly, it appears that the absorber-stripper column was installed primarily for reducing cracking requirements, by preliminary removal of hydrogen and methane in the refinery off-gas feedstocks, instead of for recovering and separating cracked gases. Furthermore, the lean oil fraction which was utilized in the absorber-stripper column consisted of 54.0% of benzene and toluene and 17.6% of pentanes and lighter hydrocarbons which are significantly lighter than the usual lean oil.

Sixthly, the specification also indicates that the process was limited to ethylene as its product and was not flexible enough to provide additional desirable by-products such as propylene, which was sent to the heaters for cracking, and acetylene, which was totally ignored in the process and also recycled. Further, other unreacted paraffins and olefin fractions heavier than ethylene were recycled to the cracking furnaces in order to make the aromatic distillate to be used as the absorber oil, even though a market existed for the propylene and undoubtedly for the butadiene at that time, thereby creating another economically wasteful aspect of the process.

As the seventh reason, the degrees of freedom for operating the Kniel process were restricted by using only temperatures and lean oil flow rates. Pressure, however, was also available as a control factor. Neglecting to use it may have led to some of the problems of the process.

Three Kniel process absorber plants had been built by the Lummus Company as of Feb. 1, 1950, according to an affidavit of Ludwig Kniel that was filed during the prosecution of Ser. No. 717,264. If confronted with high losses of absorber oil in one of these absorber plants, the designers could have taken any of several curative routes.

One such route would have been to use a higher molecular weight oil, such as the heavy ends produced in the oil-gas separators in FIG. 1 of U.S. Pat. No. 2,573,341 or the heavy ends rejected by the rerun tower, but it was known that fewer absorber molecules would then be available for absorption, thereby leading to a lower loading capacity. Lower loading capacities meant a larger solvent inventory, larger pumps, more reflux, and the like. This route was apparently rejected.

Another route would have been to adjust to the loss situation by in-plant production of absorber oil. It is known, for instance, that low partial pressure and high steam ratio maximizes olefin production and that high partial pressure and low steam ratio, plus long residence time, maximizes aromatic production. Thus it would have been a relatively simple matter to have made adjustments in the operation of the cracking furnaces for producing a desired amount of aromatics to replenish losses of absorber oil. This route was apparently taken. However, the process would have thereafter been locked into aromatic production with concomitant diminishing of ethylene production and apparent inability to compete with low-temperature fractionation processes.

The Kniel absorption process consequently seems to have suffered from the following problems:
A. wasteful burning of hydrogen, propylene, and acetylene;
B. excessive loss of aromatic absorber oil and replacement with distillate produced in the process, thereby decreasing ethylene production;
C. an apparent need for an additional column (the demethanizer) for separating methane from ethylene in order to be able to produce ethylene of sufficiently high purity; and
D. inability to economically meet increased demand for ethylene purity and recovery.

The parent patents and applications relating to the Mehra Process have utilized preferential physical solvents for recovering hydrocarbon gas liquids from natural gas streams in two embodiments: extractive flashing and extractive stripping.

The extractive flashing embodiment of the Mehra Process comprises extracting the natural gas streams with a preferential physical solvent, flashing the rich solvent, and compressing, cooling, and condensing the desired $C_2+$ hydrocarbons, as disclosed in U.S. Pat. Nos. 4,421,535, 4,511,381, 4,526,594, and 4,578,094 and in Ser. Nos. 758,351 and 759,327. The condensed hydrocarbons are then selectively demethanized to retain selected $C_2+$, $C_3+$, or $C_4+$ hydrocarbons, and the removed $C_1$, $C_1+C_2$, or $C_1+C_2+C_3$ hydrocarbons are recycled to the extraction step. The extractive flashing embodiment is described on pages 7 and 8 of the Oct. 14, 1985 issue of the Gas Processors Report, P.O. Box 33002, Tulsa, Okla. 74153.

The extractive stripping embodiment of the Mehra Process, as disclosed in Ser. Nos. 784,566, 808,463, 828,988, and 828,996, comprises contacting a raw gas stream with a preferential physical solvent in an extractive stripping column comprising an upper extraction section and a lower stripping section. The gas enters the column below the extraction section and flows upwardly where it contacts lean preferential physical solvent which, after entering the extraction section at the top of the column, flows downwardly and countercurrently to the upwardly moving gas stream. The contact takes place over mass transfer surfaces, such as packing or distillation trays. The solvent leaving the bottom of the extraction section is rich in $C_1$ and heavier hydrocarbons.

This $C_1+$-rich solvent enters the stripping section of the column and flows downwardly, where it comes in contact with the upward-flowing stripped vapors from the reboiler at the bottom of the column. The stripped vapors consist primarily of undesired components, such as methane if the desired objective is recovery of ethane and heavier hydrocarbons, or methane and ethane if the desired objective is the recovery of propane and heavier hydrocarbons, and so forth, depending upon the desired recovery objectives.

Returning to cost reduction possibilities for olefin facilities, it appears that a likely place therefor is the cryogenic chilling train in which hydrogen, methane, and ethylene fractions are separated. A system that can effect such separation via a less energy-intensive route can be useful in many existing olefin plants.

More specifically, the demethanizer column is an especially high-intensive energy user in a low-temperature fractionation plant because it requires extremely cold temperatures. An improved process that can eliminate the demethanizer column is accordingly needed.

A third area inviting improvement is the production of high-purity ethylene, at ethylene recovery levels better than 98% and at ethylene purities beyond 99.9%, in a more economical fashion by reducing energy consumption at a reasonable cost.

SUMMARY OF THE INVENTION

It is accordingly an object of this invention to provide a process for separating and recovering hydrogen to a selected degree from a gaseous stream containing olefins.

It is also an object to provide a process for separating and recovering methane to a selected degree from a gaseous stream containing olefins.

It is further an object to provide a process for separating olefin-containing gases into hydrogen, methane, and $C_2=+$ hydrocarbon products having desired specifications.

It is another object to provide a process for separating and recovering hydrogen, methane, and $C_2=+$ hydrocarbon gases from olefin-containing gas streams while incurring low solvent losses and reducing energy consumption over prior art processes.

It is additionally an object of this invention to provide an extraction plant for separating and recovering hydrogen, methane, and $C_2=+$ hydrocarbon gases from thermally cracked hydrocarbon gases and for thereby retrofitting an existing olefin production facility.

It is still further an object to provide such an extraction plant and process for use as a part of a new olefins manufacturing facility.

In accordance with these objects and the principles of this invention, it has surprisingly been discovered that a hydrogen-rich stream, a methane-rich stream, and a $C_2=+$ hydrocarbons stream, which is extremely pure with respect to methane and from which extremely pure ethylene is subsequently recoverable, can be separated and recovered from a stream of compressed, sweet, dry hydrocarbon gases, which include a substantial proportion of unsaturated hydrocarbons, by passing the hydrocarbon gas stream through two extraction columns in series, countercurrently to streams of lean preferential physical solvent, and by feeding at least one rich solvent bottoms stream to at least one distillation column which regenerates the rich solvent to form lean solvent and produces at least one of the three products. At least one extraction column is an extractive stripping column.

Each extractive-stripping column contains a stripping section, having a heat input means, and an extraction section thereabove. Either or both of the extractive-stripping columns can additionally be provided with a rectification section which is disposed above the extraction section and comprises a partial condenser which receives the overhead stream from the top of the column, an accumulator, and a reflux line to the top of the column. Each extractive stripping column is a part of a solvent loop. The same solvent can be employed in both loops.

The two extraction columns and the one or two distillation columns can be arranged according to any of three embodiments. In two of the three embodiments, the three products are recovered as, or from, overhead streams of three of the four columns. In all of these three embodiments, the stream of compressed, sweetened, and dried hydrocarbon gas is fed to the midsection of the first extraction column, which is the ethylene extraction column (EEC).

The arrangements of these embodiments, the principal content of their overhead and bottom streams, the column designations, and the solvent flow and one or two loops are shown in Table I. It can be seen that the arrangements of the extraction columns in these embodiments can be briefly described as EEC/MEC, EEC/MPC, and EEC/MEC/FV.

| FIG. No. | Streams from Each Column | First Extraction Column Stream Contents | First Extraction Column Desig. | Second Extraction Column Stream Contents | Second Extraction Column Desig. | Flash Vessel Stream Contents | Flash Vessel Ves. Desig. | First Distillation Column Stream Contents | First Distillation Column Desig. | Second Distillation Column Stream Contents | Second Distillation Column Desig. |
|---|---|---|---|---|---|---|---|---|---|---|---|
| 4 | Overhead | $H_2/CH_4$ | EEC | $H_2$ | MEC | — | — | $C_2=+$ | RPC | $CH_4$ | MPC |
| 4 | Bottoms | $C_2=+/S_1$ | EEC | $C_1/S_2$ | MEC | — | — | $S_1$ | RPC | $S_2$ | MPC |
| 5 | Overhead | $H_2$ | EEC | $CH_4$ | MPC | — | — | $C_1+$ | SRC | $C_2=+$ | RPC |
| 5 | Bottoms | $C_1+/S_1$ | EEC | $C_2=+/S_2$ | MPC | — | — | $S_1$ | SRC | $S_2$ | RPC |
| 6 | Overhead | $H_2/CH_4$ | EEC | $H_2$ | MEC | $CH_4$ | FV | $C_2=+$ | RPC | — | — |
| 6 | Bottoms | $C_2=+/S$ | EEC | $C_1/S$ | MEC | S | FV | S | RPC | — | — |

S = Solvent in Single Solvent Loop
$S_1$ = Solvent in First Solvent Loop
$S_2$ = Solvent in Second Solvent Loop
$C_2=+$ = Ethylene and heavier hydrocarbons, including saturated, unsaturated, paraffinic, and aromatic compounds.
$C_1+$ = Methane and heavier hydrocarbons, including saturated, unsaturated, paraffinic, and aromatic compounds.
EEC = Ethylene Extraction Column
MEC = Methane Extraction Column
MPC = Methane Product Column
RPC = Raw Product Column
SRC = Solvent Regeneration Column
FV = Flash Vessel In the EEC/MEC embodiment, the overhead ES stream is partially refluxed and partially fed to the MEC column, which is the methane extraction column (MEC), and the bottoms stream is fed to the first distillation column, which is the raw product column (RPC). It regenerates lean solvent for the first solvent loop and produces the product stream of $C_2=+$ hydrocarbons. The second extraction column produces the hydrogen-rich gas product stream as its overhead and a rich solvent bottoms stream which is fed to the second distillation column, identified as the methane product column (MPC). It produces the methane-rich gas product stream as its overhead and regenerated solvent for the second solvent loop as its bottoms stream.

In the EEC/MPC embodiment, the ethylene extraction column (EEC) extracts most of the methane as well as the ethylene and other $C_2+$ hydrocarbons (both saturated and unsaturated) in its rich solvent stream, producing the hydrogen-rich gas product stream as its overhead. The rich solvent stream is fed to the first distillation column (SRC) which regenerates lean solvent for the first solvent loop and produces $C_1+$ hydrocarbons as its overhead stream for feeding to the mid-section of the second extraction column, which is the methane product column (MPC). This column produces the methane-rich gas product stream as its overhead and a rich solvent stream containing the $C_2+$ hydrocarbons. This rich solvent stream is fed to the second distillation column, which is identified as the raw product column (RPC), it produces the third product stream of $C_2=+$ hydrocarbons and regenerates the lean solvent for the second solvent loop.

In the EEC/MEC/FV embodiment, the ethylene extraction column (EEC), which is an extractive stripper column, extracts the ethylene and heavier hydrocarbons into its rich solvent bottoms stream which is fed to the distillation or raw product column (RPC) wherein lean solvent is regenerated and $C_2=+$ hydrocarbons product is produced as its overhead stream. The lean solvent stream is fed to the top of the second extraction column (MEC), which generally has no stripping section but may employ one if methane and hydrogen specifications dictate the need therefor, while the overhead EEC stream is fed to its bottom. The second extraction column (MEC) may operate at a higher pressure than the EEC, but the operating pressure of the MEC must be less than the critical pressure for the gas-liquid mixture in the MEC. The MEC overhead stream is hydrogen-rich gas product. Its bottoms stream of rich solvent is flashed to produce a methane-rich gas product stream and lean solvent which is fed to the top of the ethylene extraction column.

The EEC/MEC embodiment produces one product from its extraction columns and two products from its distillation columns. The EEC/MPC embodiment produces two products from its extraction columns and one product from its distillation columns. The EEC/MEC/FV embodiment produces one product from its extraction columns, one product from its flash vessel, and the third product from its single distillation column.

The cracked gases need not be compressed to a typical pressure of 500 psig but instead need compressing only up to 300–450 psig in order to extract ethylene and heavier hydrocarbons from the typical cracked or refinery gases.

The process of this invention utilizes the Mehra Process technology concept for separating the components of a compressed, sweetened, and dehydrated cracked gas stream of an olefin facility by effectively using a preferential physical solvent for scrubbing the gas stream and preferentially removing selected hydrocarbons therefrom. Additional solvent information is given in Ser. No. 808,463, which is incorporated herein by reference.

For the purposes of this invention and illustrating the improvements over the prior art, the process begins at the low pressure inlet to the cracked gas compressor which represents the first tie-in point, since the manufacture of ethylene, i.e., the cracking process, is outside the scope of this invention. The ethylene-plus-components stream entering the de-ethanizer column, as the main product stream of this invention, represents the other tie-in point, since the downstream fractionation into individual products is also outside the scope of this invention. Other products of this invention process are a hydrogen-rich gas stream and a methane-rich gas stream. These three products, namely ethylene-plus, methane-rich and hydrogen-rich, are thereafter to be treated in the same manner as currently in the prior art.

Thus the process of this invention relates to the separation of ethylene and heavier hydrocarbons from methane and hydrogen gases present in the cracked gases of an olefins plant, refinery off-gas streams, coke-oven gas streams, or synthesis gas streams.

Since the Mehra Process concept is applicable to any gas stream containing olefins derived from any feedstock and since it addresses the separation processes which are currently energy intensive, the Mehra Process is potentially suitable for retrofitting any of the worldwide ethylene facilities, currently having 108 billion pounds per year of equivalent installed ethylene capacity.

In the olefins separation schematics of FIGS. 1 and 3, the three steps common and identical to a typical olefins facility and the process of this invention are cracking, waste heat recovery, and de-ethanizing, plus any succeeding steps in downstream equipment, such as ethylene/ethane fractionators, depropanizers, propylene/propane fractionators, debutanizers, etc.

Consumption for charge gas compression is reduced by this replacement of a low temperature fractionation plant by a Mehra Process system, because the Mehra Process extraction process does not require high pressures for separation of components. Similarly, acid gas treating and dehydration can occur at lower pressures. Dehydration needs are also considerably reduced because extreme cryogenic temperatures are never utilized in the Mehra Process for separation of desirable ethylene and heavier hydrocarbons from the cracked gas streams. Thus simple glycol dehydration may serve adequately for the utilization of the Mehra Process concept.

Since the Mehra Process extraction unit does not require extreme cryogenic temperatures, there is no need for low levels of refrigeration as provided by the ethylene and propylene refrigeration systems in a conventional low-temperature fractionation plant. The extraction unit is further capable of separating hydrogen from methane, thereby producing two separate gas streams as products. The $C_2=+$ product from the Mehra Process unit meets specifications for the lighter components, namely methane and hydrogen, of the ethylene product and is thus suitable for downstream processing in a conventional de-ethanizer.

The cracked gases leaving the waste heat recovery unit are compressed in a multi-stage compressor to a desired pressure in the range of 150 to 450 psig. The compressed gases may be optionally cooled down to a temperature of no less than $-20°$ F. prior to extraction. The cracked gases enter an Ethylene Extraction Column (EEC), which may consist only of an extraction section and a stripping section with side and bottom reboilers. This column may additionally utilize an overhead partial condenser for generating reflux for a rectification section in order to achieve extremely high recoveries, in the order of 98 to 99%, of ethylene present in the cracked gases when feedstocks and severity of cracking result in excessive amounts of methane in the cracked gases, thus minimizing the loss of valuable ethylene with the overhead stream.

Therefore, an EEC may consist of a rectification section with an overhead condenser at the very top, a middle section for extraction of ethylene and heavier hydrocarbons with a referential physical solvent, and a bottom stripping section with side and bottom reboilers. However, a simple reboiled extraction column, consisting of an extraction section at the top and a stripping section with appropriate side and bottom reboilers, may well be equally suited for desired recoveries, of course depending upon the economic optimization of parameters of capital and energy consumption.

The purpose of the extraction section is to recover ethylene and heavier hydrocarbons from the cracked gas stream entering at the bottom of the extraction section and flowing upwardly through mass transfer mediam, such as packing or fractionation trays or alternatively utilizing HIGEE TM trays, while contacting the downwardly flowing preferential physical solvent at a flow rate which is selectively adjusted from 0.001 to 0.5 gallon of the solvent per standard cubic foot of the gas stream and in response to the composition and flow rate of the gas stream. HIGEE is a trademark of Imperial Chemical Industries. During the extraction process, some of the contained methane in the cracked gases is also simultaneously recovered by the physical solvent.

The solvent stream leaving the bottom of the extraction section of the EEC is stripped of undesirable methane by effectively utilizing additional mass transfer medium in the stripping section of the column. The stripping vapors are preferably generated by heating the rich solvent stream in side and/or bottom reboilers, but they can be from an outside source of compatible gas stream. The source of heat energy can be external or waste heat as recovered through the lean solvent loop. In essence, the solvent containing ethylene and heavier hydrocarbons leaving the bottom of the stripping section of EEC does not contain more than permitted amounts of undesirable components, such as methane, in accordance with the specifications of ethylene product.

In the process of stripping undesirable components from the rich solvent and extracting the stripped vapors in conjunction with the cracked gas stream in the extraction section, the vapors leaving the top of the extraction section carry with them some of the desirable components such as ethylene, the recovery of which is desired to be in the order of 98 to 99%. Depending upon the composition of methane and hydrogen components in the cracked gas stream and relative economics of recovering ethylene under desired levels by varying the solvent flowrate to the extraction section of EEC, a rectification section may suitably be provided to effectively carry out the desired rectification, resulting in improved recoveries of the ethylene component of the cracked gas stream.

Thus, the overhead vapors are partially condensed to generate adequate amounts of reflux for the rectification section. Furthermore, the rectification section also recovers any physical solvent that may be carried away with the methane and hydrogen streams.

The solvent containing only the desired components of ethylene and heavier hydrocarbons may be further heated if economically desirable before processing in the Raw Product Column (RPC). In this column, the extracted hydrocarbons from the cracked gas stream are separated from the physical solvent. The rectification section is operated so as to minimize the solvent losses with the hydrocarbon product from the overhead of the column. The operating conditions at the top of the column are preferably such that the overhead can be condensed by available condensing media, such as air or cooling water. At the operating pressure at the bottom of the Raw Product Column, the temperature of the bottoms is generally less than the equivalent boiling temperature for pure component solvent. Generally, a small amount of heavier hydrocarbons (less than 2 mol %) may remain with the lean solvent in order to keep the size of RPC within economic criteria.

The overhead product from RPC is further processed in the de-ethanizer and downstream equipment as conventional steps. The stripped solvent from the bottom of RPC is recycled to the top of the extraction section of EEC after cooling the lean solvent to the desired temperature via a heat recovery loop and lean solvent cooler, similar to but not restrictive to the arrangement in FIG. 4.

Any liquids formed and separated at the interstage pressure levels of the cracked gas compressor may be stabilized for further processing in the fractionation train of a typical olefins plant. However, depending upon the composition and quantity of the separated stream, it may be advantageous to stabilize through the EEC. This stream, therefore, enters EEC at an appropriate location in the stripping section, preferably in between the stripping and extraction sections.

Since a Mehra Process plant does not require high pressures for extraction of ethylene plus components, it may be economically advantageous to provide a secondary but parallel extraction column operating on a common solvent loop with the first column and operating at an intermediate pressure level consistent with the desired interstage pressure of the cracked gas compressor. The obvious advantage of doing this would be to selectively extract $C_3+$ or $C_4+$ hydrocarbons from the cracked gas in order to further reduce the compression requirements of the cracked gas compressor. It would be preferred, but not necessary, to utilize an operating pressure level of the secondary parallel extraction column that is slightly higher than the operating pressure of the Raw Product Column (RPC). The rich solvent stream from the bottom of the parallel extraction column is such that it meets the same requirements of undesirable components, such as methane, as applicable to EEC, so that it can be combined together with the rich solvent stream from EEC before processing in RPC.

As an alternative, it may be more economical in some instances to recycle a small vapor stream from the top of the accumulator for RPC to the appropriate interstage of the cracked gas compressor, thereby relaxing the stringent specification for methane at the bottom of EEC. The objective in any situation should always remain its economic viability and flexibility.

The uncondensed vapors from the overhead of EEC primarily comprise hydrogen and methane. In two disclosed embodiments, this stream is then fed to the Methane Extraction Column (MEC) where methane is selectively extracted from the hydrogen-methane stream with a preferential physical solvent in solvent loop No. 2. The column is operated under stringent specifications of hydrogen content in the methane stream which is leaving through the bottom of MEC while most of the contained methane in the feed to MEC is recovered with the bottoms. Similarly, the operational objective of MEC is to maintain a low methane content in the hydrogen stream leaving the top of the column. Depending upon the specifications for the hydrogen-rich gas stream, a rectification section may advantageously be employed on top of MEC. The hydrogen product leaving MEC may be further processed before use thereof within the olefins plant, such as for hydrogenating acetylene to ethylene.

The rich solvent containing methane and remaining amounts of unrecovered ethylene is separated from the solvent in loop No. 2 by fractionating the methane in the Methane Product Column (MPC). The solvent thus stripped is recycled to the top of MEC for further extraction of methane. The solvent in loop No. 2 is treated in a similar fashion as the solvent in loop No. 1 by heat recovery and cooling to desired temperature for extraction in MEC.

It is conceivable that two different preferential physical solvents may be used in the two different solvent circulation loops. Thus, the solvent utilized in loop #2 will be relatively more selective towards methane over hydrogen when compared to similar characteristics of the solvent used in solvent loop #1. It is also satisfactory if both solvent loops use the same physical solvent. However, it is important to note that the operating conditions of flows, temperatures, and pressures may be different as required by the services.

Another advantage of this invention process is that the olefins plant becomes more flexible towards the choice of processing various feedstocks. In most of the designs, there has always been a grave concern over how much flexibility ought to be built in so as to keep the plant most economical at all times. A significant amount of restriction is caused by the limitations of the refrigeration systems and the cryogenic chill-down trains. With the use of the Mehra Process, it becomes relatively easy to provide additional feedstock flexibility. Furthermore, because of the reduction of energy utilization in the separation train, the existing plants can be made more cost effective and/or can be expanded at a nominal expense.

Under the normal operating conditions of hydrocarbon distillation systems, the alpha or relative volatility for methane over ethylene is about 5.0. However, as presented at the 59th Annual Gas Processors Association Convention, March 17–19, 1980, in a paper entitled "High $CO_2$—High $H_2S$ Removal with SELEXOL Solvent" by John Sweny, the relative volatility of methane over ethylene is 7.3. Thus, in the presence of dimethyl ether of polyethylene glycol (DMPEG), the relative volatility of methane over ethylene is considerably improved (46%) when compared to a normal fractionation system, thereby suggesting that DMPEG is selective towards the recovery of ethylene from a stream containing methane and ethylene. Since the relative behavior of methane and ethylene is altered by the presence of a preferential physical solvent such as DMPEG, the process of contact between the gas stream and the physical solvent is selective absorption or better defined as extraction instead of absorption.

The preferential physical solvents are defined for the purposes of this invention as having a minimum relative volatility of methane over ethylene of at least 5.5 (thereby defining its improved selectivity toward ethylene over methane) and in addition a solubility of at least 1.0 standard cubic foot of gaseous hydrocarbons per gallon of the solvent (SCF/GAL) (thereby defining its hydrocarbon loading capacity), or, alternatively, a preferential factor of at least 5.5. The preferential factor for physical solvent selection for using the Mehra Process concept in this invention is defined as a product of relative volatility of methane over ethylene multiplied by the solubility of ethylene in physical solvents, specified as standard cubic feet of ethylene per gallon of solvent (SCF/GAL). However, the ideal preferential physical solvent would have a selectivity toward ethylene over methane of at least 10.0 and would simultaneously possess a hydrocarbon loading capacity of at least 3.0 SCF/GAL. When an ethylene purity of at least 99.5% and ethylene recovery of 99% are required, a preferential factor of at least 7.0 is highly preferred. For obtaining an ethylene purity of at least 99.95% and an ethylene recovery of 99.5%, a preferential factor of 10.0 is highly preferred.

Additionally, the preferential physical solvent is selected from the group consisting of dialkyl ethers of polyalkylene glycol, N-methyl pyrrollidone, dimethylformamide, propylene carbonate, sulfolane, glycol triacetate, and $C_8$ to $C_{10}$ aromatic compounds having methyl, ethyl, or propyl aliphatic groups specifically constituting a sub-group of mesitylene, n-propyl benzene, n-butyl benzene, o-xylene, m-xylene, p-xylene, and mixtures thereof and aromatic streams rich in mixed xylenes and other $C_8$–$C_{10}$ aromatics.

However, the process of this invention is also able to utilize two different solvents Equipping the first extraction column with a rectification section is particularly desirable if the solvents are different.

The process of this invention produces a high-purity ethylene product at high recovery levels and also produces usefully pure product streams of hydrogen and methane. The process is additionally believed to be characterized by extremely low solvent losses, reduced maintenance requirements, simplified apparatus requirements and lower capital costs, elimination of freeze-ups, increased onstream time, enhanced flexibility, and capability of using a wide variety of feedstocks. Moreover, this process is equally capable of manufacturing propylene, with the same characteristics and advantages.

DESCRIPTION OF THE PREFERRED EMBODIMENTS

Figure 1:
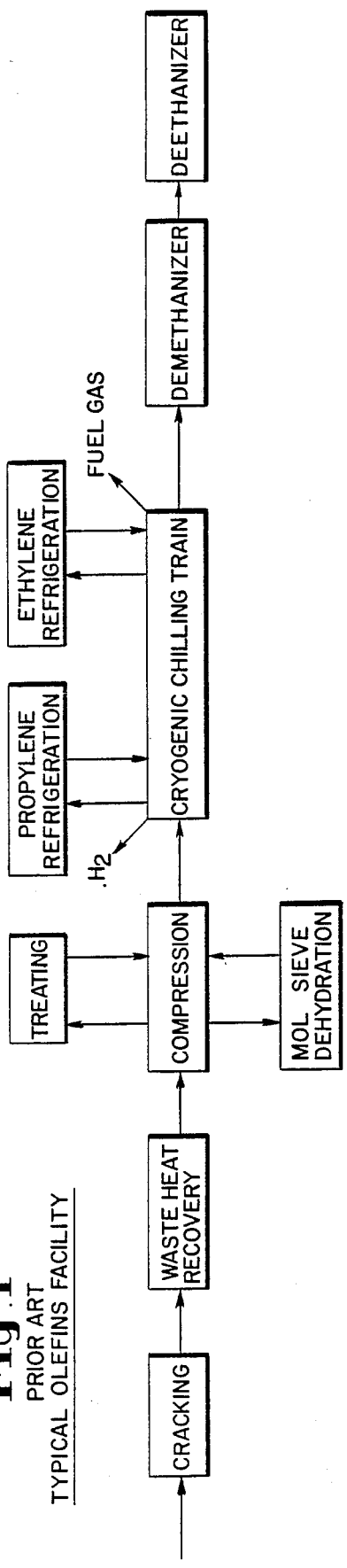
FIG. 1 is a schematic drawing for a typical olefin facility in which cracked gases are recovered and partially separated by the low-temperature fractionation process.

With reference to FIGS. 3, 4, 5, and 6, it should be understood that pipelines are in fact being designated when streams are identified hereinafter and that streams are intended, if not stated, when materials are mentioned. Moreover, flow-control valves, temperature regulatory devices, pumps, and the like are to be understood as installed and operating in conventional relationships to the major items of equipment which are shown in the drawings and discussed hereinafter with reference to the continuously operating process of this invention. All of these valves, devices, and pumps, as well as heat exchangers, accumulators, condensers, and the like, are included in the term, "auxiliary equipment". The term, "absorber", is conventionally employed for a gas/solvent absorbing facility, but when it is utilized in the process of this invention with a preferential physical solvent, it is considered to be an "extractor".

It is also to be understood that when "$C_2=+$ hydrocarbons" is mentioned, the term signifies ethylene and heavier hydrocarbons, both saturated and unsaturated and both alkyl and aromatic. Similarly, "$C_1+$" signifies methane and heavier hydrocarbons, both saturated and unsaturated and both alkyl and aromatic.

Figure 4:
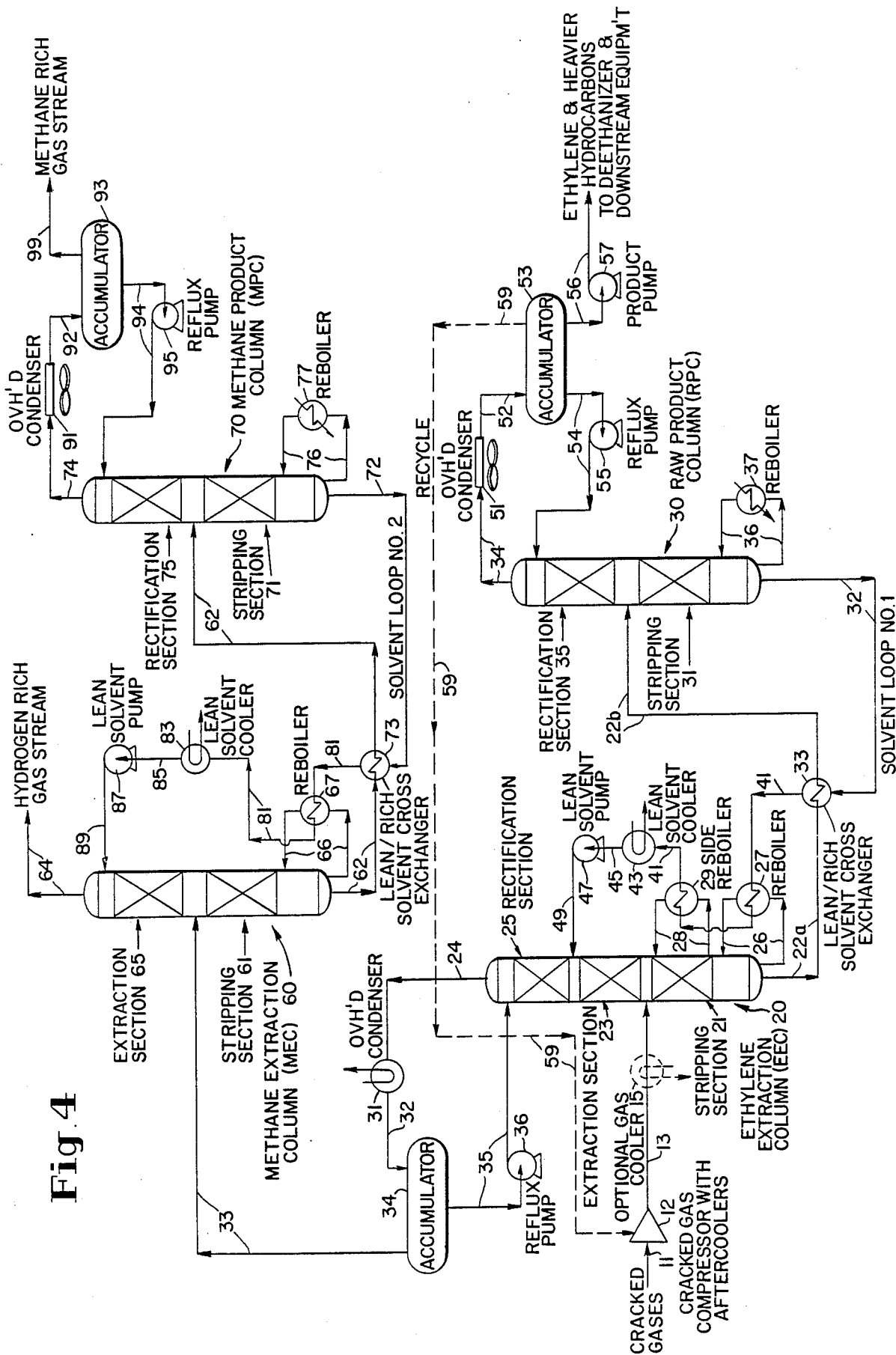
FIG. 4 is a schematic process flow diagram for recovering and separating cracked gases into a stream of hydrogen-rich gas, a stream of methane-rich gas, and a de-ethanizer feed stream by use of the Mehra process. This diagram fits into the block which is labeled "Mehra Process Extraction" in FIG. 3 so that its entire $C_2=+$ product is fed to the de-ethanizer column.

The process shown schematically in the flow sheet of FIG. 4 comprises a rectifying-extractive-stripper column referred to as the ethylene extraction column (EEC) 20 and a raw product column (RPC) 30 in the first solvent loop and a methane extraction column (MEC) 60 and a methane product column (MPC) 70 in the second solvent loop.

Cracked or refinery inlet gas stream 11 enters gas compressor 12, which is equipped with aftercoolers and systems for sweetening and dehydrating the gas. After the heavier fractions, the acidic impurities, and the water have been eliminated from the products of pyrolysis, the actual recovery of ethylene and propylene can be undertaken. With such elimination pretreatment incorporated in the compression cycle, the choice and design for the final product separation system is considerably simplified.

The compressed, cooled, sweetened, and dehydrated gas passes through line 13, selectively including optional gas cooler 15, to the midsection of EEC 20. The gas thereafter flows upwardly through extraction section 23, while flowing past the downwardly moving lean solvent from line 49, and then enters rectification section 25, while flowing past the downwardly moving reflux from line 35, and finally leaves the column through line 24 as the overhead stream.

The combined reflux and solvent pass through extraction section 23 into stripping section 21 while meeting upwardly moving vapors produced from bottoms liquid, after it has been heated by recycling through line 26 and reboiler 27, and from intermediate liquid, after it has been heated by recycling through line 28 and side reboiler 29. A portion of the upwardly moving vapors is extracted by the combined reflux/solvent liquid. The remaining vapors rise to the extraction section and mix with the incoming gas stream from line 13. The hot bottoms liquid from the column is discharged through line 22a, passes through lean/rich solvent cross exchanger 33, and is then fed through line 22b to the midsection of RPC 30.

Column 30 comprises a stripping section 31 and a rectification section 35. The upwardly moving gases pass through rectification section 35, while encountering downwardly moving lean solvent from reflux line 54, and leave the system as the overhead stream through line 34, to be condensed in overhead condenser 51, pass through line 52, and enter accumulator 53 from which a portion is recycled to the top of RPC 30 by reflux pump 55 through line 54, while another portion is pumped by product pump 57 through line 56 to produce ethylene and heavier hydrocarbons to be fed to the de-ethanizer and other downstream equipment. Another portion of uncondensed gases may be selectively recycled, if economical to do so, through line 59 to cracked gas compressor 12.

The refluxed hydrocarbons in line 54 of loop No. 1, containing traces of solvent, move downwardly, countercurrently to the upwardly moving gas stream from line 22, through rectification section 35 and enters stripping section 31 while meeting upwardly moving vapors therewithin which are produced by passing the bottoms liquid through recycle lines 36 and reboiler 37. The purpose of rectification section 35 is to reduce solvent losses with the $C_2=+$ hydrocarbon product. The heated bottoms material in the bottom of RPC 30 is discharged through line 32 of the return portion of solvent loop No. 1 to pass through lean/rich solvent cross exchanger 33, line 41, reboiler 27, side reboiler 29, lean solvent cooler 43, line 45, line 41, lean solvent pump 47, and feed line 49 to the top of extraction section 23 of EEC 20.

Overhead stream 24 passes through overhead condenser 31 and line 32 to enter accumulator 34 from which liquid is recycled through line 35 by reflux pump 36 to the top of rectification section 25 in EEC 20. The first solvent loop and its columns and auxiliary equipment are thus completely described.

Uncondensed gases in accumulator 34 are passed through feed line 33 to the midsection of methane extraction column (MEC) 60, between stripping section 61 and extraction section 65. The gases from line 33 pass upwardly through extraction section 65, while meeting lean solvent from line 89, and leave the column as a hydrogen-rich gas product stream 64. The downwardly descending lean solvent from line 89 passes through extraction section 65, while effectively picking up materials from the gas stream entering through line 33, and enters stripping section 61, while meeting ascending vapors and picking up methane therefrom and while losing hydrogen to the vapors. The liquid bottoms material in the column is heated by recycling through line 66 and reboiler 67. The bottoms material in the column is discharged through lines 62a and 62b, and lean/rich solvent cross exchanger 73 to be fed to the midsection of MPC 70.

Column 70 comprises a stripping section 71 and a rectification section 75. The gases, which have been heated in exchanger 73, pass upwardly through rectification section 75 while meeting downwardly descending reflux material from line 94. The overhead stream from the column leaves through line 74, overhead condenser 91, and line 92, to enter accumulator 93. From this accumulator, liquid material is recycled through lines 94 and reflux pump 95 to the top of rectification section 75 of MPC 70. Vapor from accumulator 93 is discharged as a methane-rich gas stream through line 99.

The descending reflux liquid picks up solvent in loop No. 2, while giving up methane and any $C_2=+$ hydrocarbons during its passage through rectification section 75, and then enters stripping section 71 wherein it encounters upwardly moving vapors from the heated bottoms material in the column. Heating of this material is accomplished by recycling it through line 76 and reboiler 77. The heated bottoms material, now lean solvent, is discharged through line 72 to pass through lean/rich solvent cross exchanger 73, line 81, reboiler 67, lean solvent cooler 83, line 85, lean solvent pump 87, and feed line 89 to the top of extraction section 65 of MEC 60. The second solvent loop and its columns and associated equipment are thus completely described.

In summary, the purpose of EEC 20 is to selectively extract all hydrocarbon components of inlet gas stream 13 by effectively utilizing the selectivity of the preferential physical solvent in stream 49. The purpose of RPC 30 is to remove all hydrocarbon components of the inlet gas stream that are present in rich solvent stream 22b and produce the lean solvent stream in line 32 plus the product stream of $C_2=+$ hydrocarbon components present in overhead stream 34.

The purpose of MEC 60 is to isolate most of the hydrogen as its overhead stream in line 64 and to isolate most of the methane as a part of the rich solvent stream in line 62a. The purpose of MPC 70 is to isolate substantially all of the remaining methane in methane-rich gas stream 99, which includes small quantities of $C_2$ and $C_3$ hydrocarbons, and to regenerate the lean solvent in stream 72.

FIG. 4 shows a system in which two entirely different preferential physical solvents may be used, if so desired, in two solvent loops. The first or primary loop is directed to separating of $H_2$ and $CH_4$ in its overhead stream from $C_2=+$ hydrocarbons in its rich solvent stream and then to recovering $C_2=+$ hydrocarbons and regenerating the solvent. The second or secondary loop is directed to recovery of a hydrogen-rich gas stream and then to recovery of a methane-rich gas stream while regenerating the solvent. The two loops are connected by the overhead stream from the first loop being the feed gas stream for the second loop.

When using two different preferential physical solvents in the two different solvent circulation loops, the solvent utilized in loop No. 2 of FIG. 4 will be relatively more selective towards methane over hydrogen when compared to similar characteristics of the solvent used in solvent loop No. 1. Such a first solvent is preferably an aromatic distillate, such as mesitylene or a $C_8$–$C_{10}$ monocyclic aromatic having at least one alkyl side chain and having a lower boiling point and a higher preferential factor than the solvent in the second loop which may be dimethyl ether of polyethylene glycol (DMPEG), for example.

If the same preferential physical solvent is used in both solvent loops, $C_8$–$C_{10}$ moncyclic aromatic solvents are preferred. However, it is important to note that the operating conditions of flows, temperatures, and pressures may be different as required by the services.

Each loop passes through two columns, one column being an extractive stripping column and the other column being a distillation column. Each extractive stripping column has at least a stripping section and/or a rectification section and/or an extraction section. Each of the four columns is also equipped with a reboiler for heating its bottoms material. The first column of each loop is an extractive stripping column, and control of its performance is partially effected by control of the temperatures and flow rates of the lean solvent streams being fed to the upper portions of the columns. Preferably, the first column of the first section is additionally provided with reflux which is fed to the column at a feed point spaced above the feed point for the lean solvent stream, thus defining a rectification section therebetween. The second extractive stripping column is preferably not provided with reflux, but may have it if fairly pure hydrogen is desired. The second column of each loop is a product column, the first one being for isolating raw $C_2=+$ hydrocarbons as its overhead stream and the second one being for isolating impure methane as its overhead stream.

Figure 5:
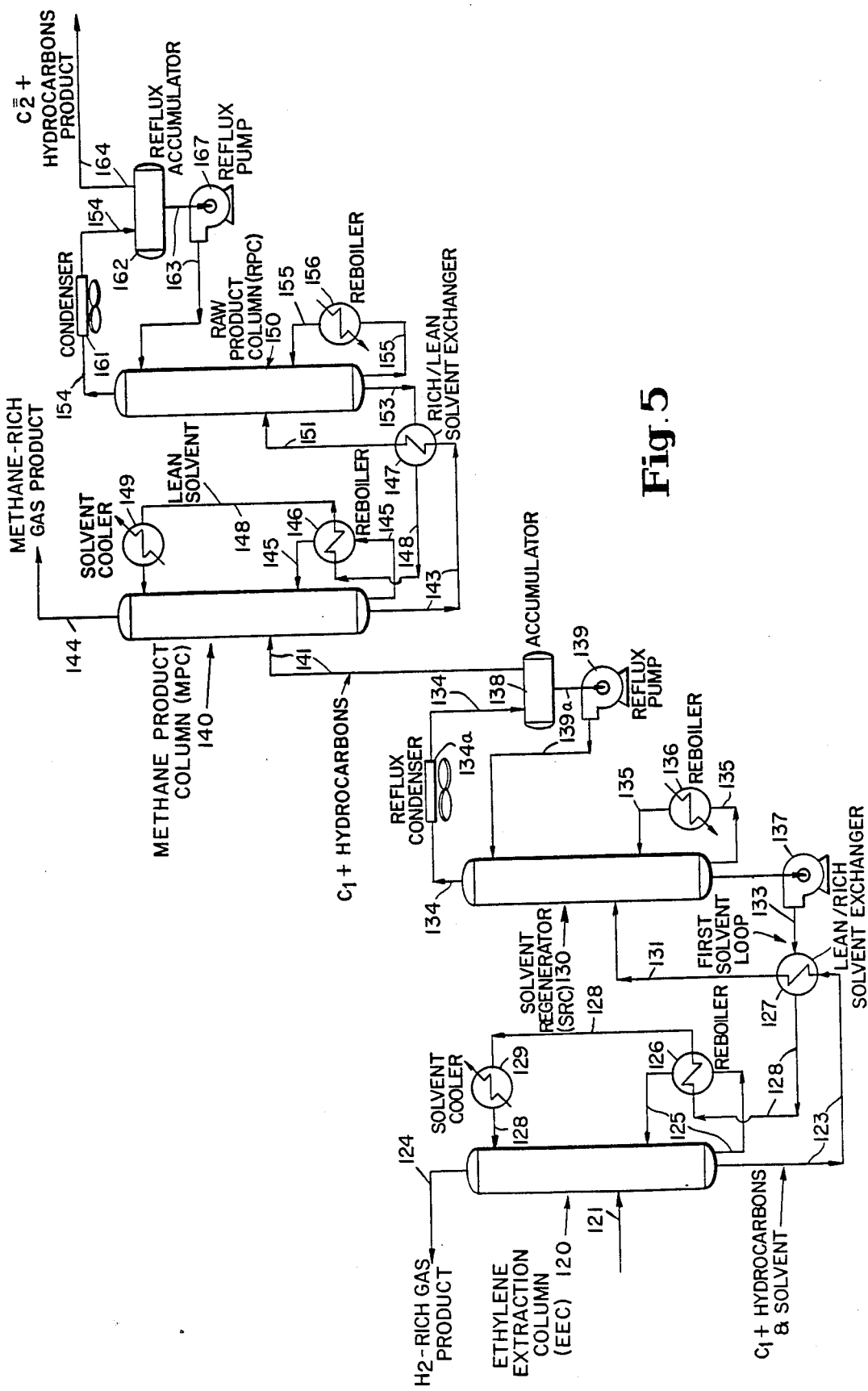
FIG. 5 is a schematic flowsheet showing another embodiment of the Mehra Process in which an ethylene extraction column (EEC) extracts all of the hydrocarbons into its rich solvent stream to form a hydrogen-rich gas stream as the first product, a methane product column (MPC) extracts the ethylene and heavier hydrocarbons into its rich solvent stream to form a methane-rich gas stream as the second product, and a raw product column (RPC) receives the MPC bottoms to produce a $C_2=+$ hydrocarbons product stream as the third product.

FIG. 5 illustrates a two-column extractive-stripping process for a gas stream containing olefins, for example, in which there is initial separation of the hydrogen from all of the hydrocarbon components within the first column. This process utilizes ethylene extraction column (EEC) 120, solvent regenerator column (SRC) 130, methane product column (MPC) 140, and raw produot oolumn (RPC) 150.

Compressed, sweetened, cooled, and dry gas enters column 120, slightly below its middle, through line 121. Liquid in the bottom of the column circulates through line 125 and reboiler 126 to be heated. Bottoms in column 120 leave through line 123 and solvent exchanger 127. Overhead from column 120 leaves through line 124 as hydrogen-rich gas product.

The heated rich solvent in exchanger 127 passes through line 131 to enter column 130, slightly below its middle. Liquid in the bottom of column 130 circulates through line 135 and reboiler 136 to be heated. Bottoms from column 130 leave through line 133 and pump 137 to enter heat exchanger 127 and pass through line 128, reboiler 126, and solvent cooler 129 to enter the top of column 120 as lean solvent.

An overhead stream leaves column 130 through line 134, is cooled in reflux condenser 134a, enters accumulator 138, and separates into uncondensed and condensed hydrocarbons. The latter leave through line 139a, are pumped by reflux pump 139 to the pressure of column 130, and enter the top of column 130 as reflux. The uncondensed hydrocarbons leave accumulator 138 through line 141 to enter column 140, slightly below its middle. Liquid in the bottom of column 140 circulates through line 145 and reboiler 146 to be heated. Bottoms leave column 140 through line 143 to enter rich/lean solvent exchanger 147 for heating therein. An overhead stream of $C_1$ gas product leaves the top of column 140 through line 144.

Heated solvent leaves exchanger 147 through line 151 and enters column 150, slightly below its middle. Liquid in the bottom of column 150 circulates through line 155 and reboiler 156 to be heated. Bottoms leave column 150 through line 153, are cooled in exchanger 147, pass through line 148 and reboiler 146, and are further cooled in solvent cooler 149 before entering the top of column 140. An overhead stream leaves the top of column 150 through line 154 and is partially condensed in condenser 161 before entering reflux accumulator 162. Condensed liquid in accumulator 162 leaves through line 163 and is pumped by reflux pump 167 to the top of column 150. Uncondensed hydrocarbons in reflux accumulator 162 leave through line 164 to become $C_2=+$ hydrocarbons product.

Figure 6:
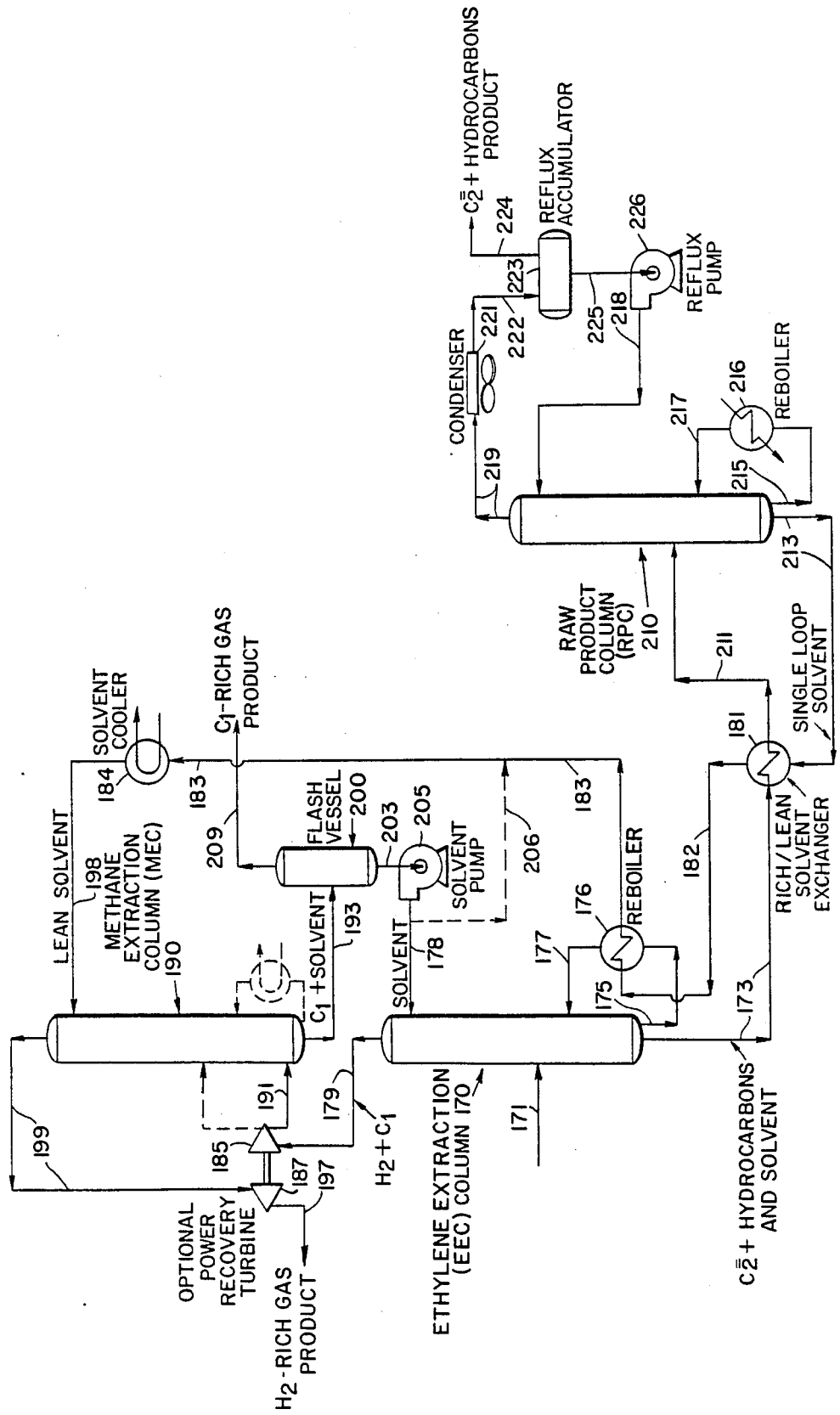
FIG. 6 is a schematic flowsheet showing a third embodiment of the Mehra process in which ethylene extraction (EEC) column separates the hydrogen and methane from its rich solvent containing the ethylene and heavier hydrocarbons. The $H_2/CH_4$ overhead stream is again extracted with lean solvent to recover an $H_2$-rich gas stream and produce a methane-rich bottom stream which is flashed to recover a $CH_4$-rich gas stream.

FIG. 6 illustrates a separation and recovery process for a gas containing olefins which has been compressed, cooled, sweetened, and dried. The process utilizes two extraction columns which may be disposed as separate columns or superimposed as a single tall column. These are a first or bottom ethylene extraction column (EEC) 170 and a second or top column (MEC) 190. The process also utilizes a flash vessel (FV) 200 and a raw product column (RPC) 210.

The inlet gas stream in line 171 enters EEC 170, slightly below its middle, and passes upwardly to meet downwardly descending lean solvent from line 178. Liquid in the bottom of column 170 circulates through line 175, and reboiler 176, and line 177 to be heated and returned to column 170. Bottoms in column 170 leave through line 173 to enter and be heated in rich/lean solvent exchanger 181. An overhead stream in line 179 leaves the top of column 170, passes through optional compressor 185 and line 191, and enters MEC 190 near its bottom. A reboiler, however, may initially be employed in order to obtain an additional stripping section below the feed location which is slightly below the middle of the column.

Bottoms leave column 190 through line 193 to enter flash vessel 200, wherein the bottoms are separated into a methane-rich gas product stream, which leaves vessel 200 through overhead line 209, and a bottoms stream which leaves vessel 200 through line 203 and solvent pump 205 before entering the top of column 170 through line 178. An overhead stream leaves the top of column 190 through line 199 and passes through optional power recovery turbine 187 to leave as a hydrogen-rich gas product stream in line 197.

Heated rich solvent leaves exchanger 181 through line 211 and enters RPC 210, slightly below its middle. Liquid in the bottom thereof circulates through line 215, reboiler 216, and line 217 to be heated and returned to column 210. Bottoms leave column 210 through line 213 and are cooled in exchanger 181. Lean solvent leaves exchanger 181 through line 182, is cooled in reboiler 176, passes through line 183, is further cooled in solvent cooler 184, and enters the top of MEC 190 through line 198. An overhead stream leaves RPC 210 through line 219, is condensed by condenser 221, and enters reflux accumulator 223, through line 222 wherein it is separated into liquid and vapor portions. The liquid portion leaves through line 225 and is pumped by reflux pump 226 through line 218 to enter the top of column 210. The vapor portion leaves through line 224 to become $C_2=+$ hydrocarbon product which is conveniently condensed.

Depending upon the relative concentrations of $H_2$ and $CH_4$ versus ethylene and heavier hydrocarbon components, the solvent requirements for EEC 170 may be significantly lower than those for MEC 190. Therefore, it may be economically desirable to bypass a substantial portion of solvent in line 178 via line 206 to lean solvent line 183. By doing so the equipment sizes for EEC 170 and a portion of the solvent loop, including units 176, 181, 210, 216, 221, 223, and 226 and their associated piping can be significantly reduced.

EXAMPLE

Figure 3:
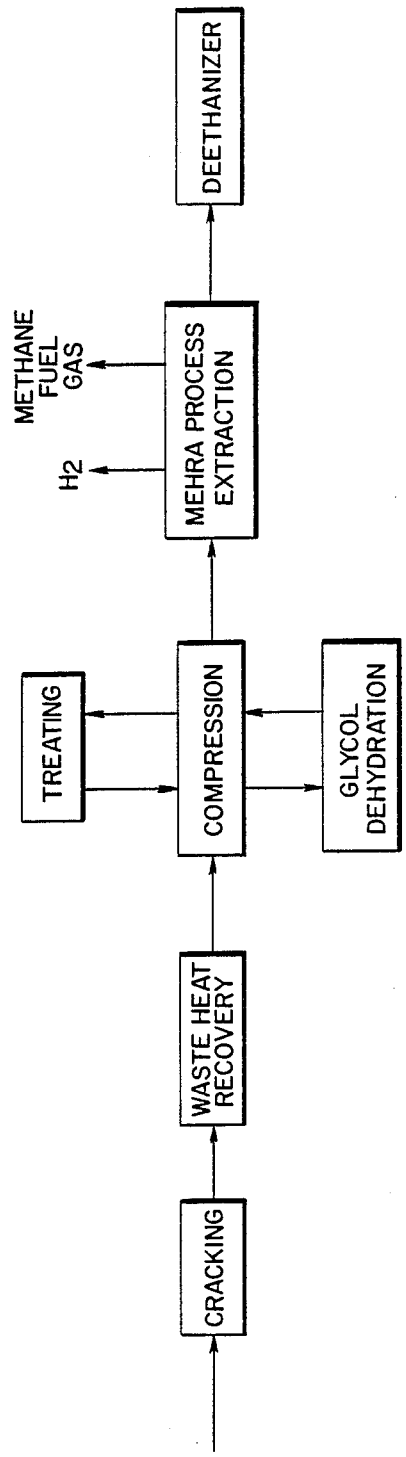
FIG. 3 is a simplified schematic drawing showing the process of FIG. 1 with the Mehra process, for recovering and separating cracked and/or refinery gases by solvent extraction, substituted for the cryogenic chilling train and demethanizer of FIG. 1.
Figure 2:
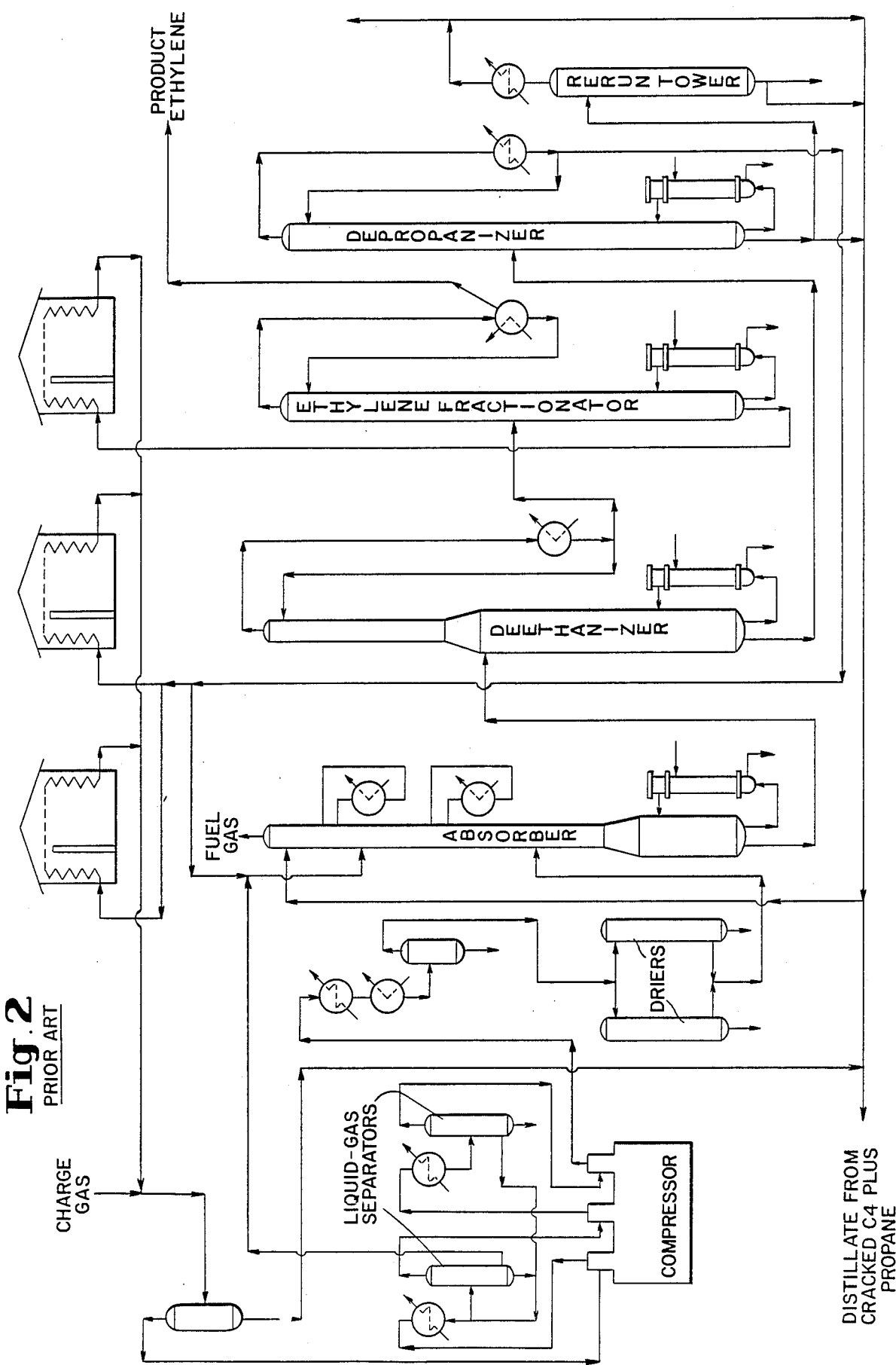
FIG. 2 is a schematic drawing of an older olefin facility showing the Kniel process of U.S. Pat. No. 2,573,341 for recovery and separation of cracked gases by solvent absorption.

An existing olefins facility, as shown in FIG. 1, is investigated for upgrading by replacing the chilling train and the demethanizer column with a Mehra process extraction system, as illustrated in FIG. 3. Portions of the propylene refrigeration system are to be retained for use with the Mehra Process extraction units. The ethylene refrigeration system can be shut down, thereby further reducing the load on the propylene refrigeration system. Replacement of the molecular sieve or dehydration unit of FIG. 1 with the glycol dehydration unit of FIG. 3 is to be considered on a basis of cost effectiveness, but for purposes of this example, it is assumed that the molecular sieve units stay in service. The Mehra process extraction system, using o-xylene as one of the preferential physical solvents, is as shown in FIG. 6.

By utilizing a commercially available and reliable computer design, the specific process of FIG. 6 was simulated. The operating conditions were only partially optimized and do not reflect a final design. In this simulation, a stream of thermally cracked olefin-containing gases, which had been compressed, cooled, sweetened, and dehydrated, was assumed to be entering EEC 170 through line 171 at 18,979.30 lb-mols/hr at 90° F. and 400 psia. A stream of lean solvent was also assumed to be entering EEC 170 through line 178 and flowing at 34,277.64 lb-mols/hr at 8.33° F. and 450 psia. Three products were calculated as recovered: 4,296.90 lb-mols/hr of hydrogen-rich gas product in line 199, 3,823.00 lb-mols/hr of methane-rich gas product in line 209, and 10,873.91 lb-mols/hr of ethylene and heavier hydrocarbons product in line 224. The compositions, other flow rates, temperatures, and pressures are given in Table II. The composition of the cracked feedstock in line 171 is typical of a thermally cracked 70/30 ethane/propane mixture on a liquid volume basis.

Product Purities

The composition of the hydrogen-rich gas product in line 199 should be noted because its hydrogen content is 93.4% on a lb-mol basis. Furthermore, its solvent content is merely 0.0017% on a lb-mol basis and its ethylene content is essentially zero.

The composition of the methane-rich gas product in line 209 is also noteworthy because its methane content is 89.5% on a lb-mol basis. In addition, its solvent content is 0.04% on a lb-mol basis and its ethylene content is 0.043% on a lb-mol basis.

The composition of the stream of ethylene and heavier hydrocarbons in line 224 is 56.3% ethylene, 22.3% ethane, and 0.030% methane on a lb-mol basis. Its o-xylene content is 0.0032% on a lb-mol basis.

Recycle Ratio

Assuming that all compounds other than hydrogen, methane, ethylene, benzene, and toluene were to be recycled from the Mehra Process system and returned to the heaters for further cracking, the recycle ratio would be 1.8, as compared to the recycle ratio of 1.0 in the Kniel absorption process according to U.S. Pat. No. 2,573,341. It is believed that this favorable recycle ratio is the result of choosing ethylene-favorable reaction conditions, as compared to aromatics-favorable reaction conditions, as were apparently required by the Kniel process.

TABLE II

| | MATERIAL BALANCE | | | | | | | | |
|---|---|---|---|---|---|---|---|---|---|
| | STREAM NUMBER | | | | | | | | |
| DESCRIPTION | 171 | 209 | 199 | 224 | 198 | 178 | 179 | 173 | 193 |
| Temperature, F. | 90.00 | 7.41 | −1.49 | 69.31 | 0.00 | 8.33 | 8.73 | 215.00 | 2.51 |
| Pressure, psia | 400.00 | 25.00 | 750.00 | 200.00 | 750.00 | 450.00 | 400.00 | 400.00 | 750.00 |
| Molecular Wt | 22.16 | 14.67 | 3.00 | 32.35 | 106.16 | 105.48 | 8.71 | 88.28 | 96.37 |
| Flow Rates LB-Mols/HR | | | | | | | | | |
| Hydrogen | 4398.00 | 392.59 | 4014.00 | .00 | 0.00 | 2.18 | 4408.80 | .00 | 394.77 |
| Methane | 3677.70 | 3420.00 | 262.29 | 3.31 | 0.00 | 254.85 | 3937.10 | 3.31 | 3674.80 |
| CO | 27.70 | 7.21 | 20.54 | .00 | 0.00 | 0.12 | 27.88 | .00 | 7.34 |
| Acetylene | 53.10 | .00 | .00 | 53.08 | 0.00 | .00 | .00 | 53.08 | .00 |
| Ethylene | 6123.20 | 1.66 | .00 | 6119.30 | .00 | 0.82 | 2.48 | 6119.30 | 2.48 |
| Ethane | 2422.70 | 0.01 | .00 | 2421.80 | 0.00 | .00 | 0.01 | 2421.80 | 0.01 |
| Propyne | 35.40 | .00 | .00 | 35.39 | .00 | .00 | .00 | 35.39 | .00 |
| Propylene | 1398.00 | .00 | .00 | 1397.50 | 0.00 | .00 | .00 | 1397.50 | .00 |
| Propane | 259.90 | .00 | .00 | 259.80 | .00 | .00 | .00 | 259.80 | .00 |
| 1,3 Butadiene | 208.50 | .00 | 0.00 | 208.42 | 0.00 | .00 | .00 | 208.42 | .00 |
| 1-Butene | 257.90 | .00 | .00 | 257.80 | .00 | .00 | .00 | 257.80 | .00 |
| N—Butane | 27.50 | .00 | .00 | 27.49 | .00 | .00 | .00 | 27.49 | .00 |
| N—Pentane | 68.40 | .00 | 0.00 | 68.38 | 0.00 | .00 | .00 | 68.38 | .00 |
| N—Hexane | 3.10 | .00 | .00 | 3.10 | .00 | .00 | .00 | 3.10 | .00 |
| N—Heptane | 3.00 | .00 | .00 | 3.00 | 0.01 | 0.01 | .00 | 3.01 | 0.01 |
| N—Octane | 3.00 | .00 | .00 | 3.01 | 7.58 | 7.58 | .00 | 10.59 | 7.58 |
| Benzene | 12.00 | .00 | .00 | 12.00 | .00 | .00 | .00 | 12.00 | .00 |
| Toluene | 0.20 | .00 | .00 | 0.20 | 0.07 | 0.07 | .00 | 0.27 | 0.07 |
| O—Xylene | 0.00 | 1.55 | 0.07 | 0.35 | 34013.00 | 34012.00 | 0.41 | 34014.00 | 34014.00 |
| TOTAL LB-MOLS/HR | 18979.30 | 3823.02 | 4296.90 | 10873.91 | 34020.66 | 34277.64 | 8376.67 | 44895.22 | 38101.06 |

Significance of Calculations

The results shown in Table II are believed to be extremely significant because the commercially available simulation package utilized for this example is routinely used for plant design.

The results shown in Table II also reveal that the Mehra Process accomplishes what the prior art does not and has not accomplished. Such previously unattainable results demonstrate that this embodiment of the Mehra Process represents a discovery of the first magnitude for the ethylene manufacturing art.

One may compare, for example, the losses of solvent which plagued the Kniel absorption process with the losses shown in Table II. Streams 199, 209, and 224, all of the streams leaving the system, show a total loss of o-xylene amounting to 1.97 lb-mols/hr. The total amount of o-xylene in stream 198 is 34,013.00 lb-mols/hr. This loss, expressed as a percentage of total o-xylene flow, equals a mere 0.006% on a lb-mol basis, a phenomenal achievement in the solvent absorption art. If mesitylene should be utilized as a preferential physical solvent as in this example, the anticipated solvent losses would be significantly lower than those of o-xylene.

Another possible comparison is on a methane rejection basis by referring to the 1947 article in *Chemical Engineering Progress* which states that the methane retained in the fat oil represented 4% of the ethylene in the cracked gas in which the volumes of methane and ethylene were almost equal. In contrast, the methane in streams 173 and 224 equals 3.31 lb-mol/hr which is 0.05% of the ethylene in stream 171, wherein the volume of methane is ⅔ the volume of ethylene.

Purity of Ethylene Product

The raw hydrocarbon product is further fractionated downstream into ethylene and ethane. Doing so while obtaining sufficiently high purity in the overhead ethylene stream requires a high performance level in the ethylene fractionator column.

As is clear from Table II, at about 72 mol % ethylene in a feedstream to an ethylene fractionator column containing only ethylene and ethane, as in stream 224, an ethylene product, with purity of 99.95 mol % and at a recovery level of 99.94%, could be produced. This performance the Kniel process could not achieve even while utilizing a demethanizer column, yet such a column is plainly not required by the Mehra Process.

Because it will be readily apparent to those skilled in the art of treating hydrocarbon gases that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. In an olefin producing facility, comprising: (a) cracking furnaces, heat recovery systems, compressor, acid gas treatment systems, and dehydration systems to produce cooled, compressed, sweetened, and dehydrated cracked gases, (b) a low-temperature fractionation train to separate and recover hydrogen, methane, and $C_2=+$ hydrocarbons from said cracked gases, and (c) a distillation train to produce ethylene and propylene as products from said $C_2=+$ hydrocarbons, the improvement comprising:

A. the replacement of said low-temperature fractionation train with an extractive stripping plant employing a preferential physical solvent which is selective for ethylene and heavier hydrocarbon components of said $C_2=+$ hydrocarbons such that the relative volatility of methane over ethylene is at least 5.5 and the solubility of ethylene in said solvent is at least 1.0 standard cubic foot of ethylene per gallon of said solvent, or the preferential factor is at least 5.5; and B. operating said extractive stripping plant according to the following steps:

(1) feeding a stream of lean preferential physical solvent at a selected flow rate and a stream of said cooled, compressed, sweetened, and dehydrated cracked gases to a first exractive stripping column having a stripping section and an extraction section and producing therefrom:

(a) a first overhead gas stream and
(b) a first bottoms stream of rich solvent,
(2) feeding said rich solvent stream to a first distillation column and producing therefrom said stream of lean physical solvent and an overhead stream of said $C_2=+$ hydrocarbons,
(3) feeding a stream of lean preferential physical solvent and said first overhead gas stream from said first extractive stripping column to a second extractive stripping column having a stripping section and an extraction section and producing therefrom:
(a) a hydrogen-rich gas stream as a second overhead gas stream and (b) a second bottoms stream of rich solvent, and
(4) feeding said second bottoms stream from said second extractive stripping column to a second distillation column and producing therefrom an overhead stream of methane-rich gas.

2. The improved process of claim 1, wherein said first extractive stripping column is a rectifying-extracting-stripping column which has a partial overhead condenser for said overhead stream thereof and reflux means for returning condensed liquid to said column at a feed point above the feed point for said preferential physical solvent, thereby defining a rectification section above said extraction section.

3. The improved process of claim 2, wherein said rectifying-extracting-stripping column is operated at less than 450 psig and wherein said flow rate of said preferential phsyical solvent in said substep 1 of said step B is selectively adjusted from 0.001 to 0.5 gallon per standard cubic foot of said cracked gas stream and in response to the composition and flow rate of said cracked gas stream.

4. The improved process of claim 1, wherein said preferential physical solvent is selected from the group consisting of dialkyl ethers of polyalkylene glycol, N-methyl pyrrolidone, dimethylformamide, propylene carbonate, sulfolane, glycol triacetate, and $C_8$ and $C_{10}$ aromatic compounds having methyl, ethyl, or propyl aliphatic groups specifically constituting a sub-group of o-xyloene, m-xylene, p-xylene, hemimellitene, pseuodcumene, mesitylene, cumene, o-ethyltoluene, m-ethyltoluene, p-ethyltoluene, n-propylbenzene, isopropylbenzene, indane, durene, isodurene, prehnitene, crude xylenes, toluene transalkylation reaction effluents, extracted $C_9$ haphtha reformates, extracted $C_9$ catalytic reformates, $C_9$ heart cuts of said reformates which are enriched in $C_9$ alkbenzenes, $C_7$–$C_9$ alkyl aromatics, and mixtures thereof.

5. The improved process of claim 1, wherein said first bottoms stream is heated by lean/rich solvent cross exchanging with said stream of lean preferential physical solvent from said first distillation column.

6. The process of claim 1, wherein said cracked gases are selected from the group consisting of thermally cracked hydrocarbon gas, catalytically cracked hydrocarbon gas, refinery off-gas, coke-oven gas, and synthesis gas.

7. The process of claim 1, wherein said preferential factor is at least 7.0.

8. The process of claim 1, wherein said preferential factor is at least 10.0.

9. The process of claim 1, wherein each said lean solvent stream flows as part of a solvent loop, said first extractive-stripping column containing a portion of a first solvent loop and said second extractive stripping column containing a portion of a second solvent loop.

10. The process of claim 9, wherein said solvent in said first solvent loop and said solvent in said second solvent loop are the same preferential physical solvent.

11. The process of claim 9, wherein said solvent in said first solvent loop and said solvent in said second solvent loop are different preferential physical solvents.

12. In a process for operating an olefins producing facility, comprising: (a) cracking furnaces, heat recovery systems, compressors, acid gas treatment systems, and dehydration systems to produce cooled, compressed, sweetened, and dehydrated cracked gases, (b) a low-temperature fractionation train to separate and recover hydrogen, methane, and $C_2=+$ hydrocarbons from said cracked gases, and (c) a distillation train to produce ethylene and propylene as products from said $C_2=+$ hydrocarbons, the improvement comprising the replacement of said low-temperature fractionation train with an extractive stripping plant employing a preferential physical solvent in two solvent loops, each loop consisting essentially of an extractive stripping column, a distillation column, and auxiliary equipment through which said solvent passes, each said extractive stripping column comprising an extractive section and a stripping section and said solvent being selective for ethylene and heavier hydrocarbon components of said cracked gases such that the relative volatility of methane over ethylene is at least 5.5 and the solubility of ethylene in said solvent is at least 1.0 standard cubic foot of ethylene per gallon of said solvent or the preferential factor is at least 5.5.

13. The improved process of claim 12, wherein said cracked gases are selected from the group consisting of thermally cracked hydrcarbon gas, catalytically cracked hydrocarbon gas, refinery off-gas, coke-oven gas, and synthesis gas.

14. The improved process of claim 12, wherein said preferential factor is at least 7.0.

15. The improved process of claim 12, wherein said preferential factor is at least 10.0.

16. The improved process of claim 12, wherein said extractive stripping plant is operated according to the following steps:

A. feeding one said stream of lean preferential physical solvent to a first extractive stripping column, having a stripping section and an extraction section, at a selected flow rate and also feeding a stream of said cooled, compressed, sweetened, and dehydrated cracked gases to said column and producing therefrom:
(1) a first overhead gas stream and
(2) a first bottoms stream of rich solvent,
B. feeding said first bottoms stream to a first distillation column and producing therefrom said stream of lean physical solvent and an overhead stream of said $C_2=+$ hydrocarbons; and
C. feeding a stream of lean preferential physical solvent and said first overhead gas stream from said first extractive stripping column to a second extractive stripping column having a stripping section and an extraction section and producing therefrom:
(1) a hydrogen-rich gas stream as a second overhead gas stream and
(2) a second bottom stream of rich solvent; and
D. feeding said second bottoms stream from said second extractive stripping column to a second distillation column and producing therefrom an overhead stream of methane-rich gas and a regenerated lean solvent stream.

17. The process of claim 16, wherein said ethylene produced by said distillation train from said stream of $C_2=+$ hydrocarbons has a purity of up to 99.5%.

18. The process of claim 16 wherein up to 99.5% of said ethylene in said stream of cracked gases is recovered.

19. The improved process of claim 12, wherein said first extractive stripping column is a rectifying-extracting-stripping column which has partial overhead condenser for said overhead stream thereof and reflux means for returning condensed liquid to said column at a feed point above the feed point for said preferential physical solvent, thereby defining a rectification section above said extraction section.

20. The improved process of claim 19, wherein said rectifying-extracting-stripping column is operated at less than 450 psig and wherein said selected flow rate of said stream of preferential physical solvent is selectively adjusted from 0.001 to 0.5 gallon per standard cubic foot of said cracked gas stream and in response to the composition and flow rate of said cracked gas steam.

21. The process of claim 12, wherein said preferential physical solvent is selected from the group consisting of dialkyl ehters of polyalkylene glycol, N-methyl pyrrolidone, dimethylformamide, propylene carbonate, sulfolane, glycol triacetate, and $C_8$ to $C_{10}$ aromatic compounds having methyl, ethyl, or propyl aliphatic groups specifically constituting a sub-group or o-xylene, m-xylene, p-xylene, hemimellitene, pseudocumene, mesitylene, cumene, o-ethyltoluene, m-ethyltoluene, p-ethytoluene, n-propylbenzene, isopropylbenzene, indane, durene, isodurene, prehnitene, crude xylenes, toluene transalkylation reaction effluents, extracted $C_9$ naphtha reformates, extracted $C_9$ catalytic reformates, $C_9$ heart cuts of said reformates which are enriched in $C_9$ alkybenzenes, $C_7$-$C_9$ alkyl aromatics, and mixtures thereof.

22. The improved process of claim 12, wherein said rich solvent stream is heated by lean/rich solvent cross exchanging with said stream of lean preferential physical solvent.

23. The process of claim 12, wherein said solvent in one said solvent loop and said solvent in the other said solvent loop are the same preferential physical solvent.

24. The process of claim 12, wherein said solvent in one said solvent loop and said solvent in the other said solvent loop are different physical solvents.

25. A process for treating a feed stream of hydrogen, methane, and $C_2=+$ hydrocarbons, comprising the following steps:
A. contacting said feed stream with a stream of a lean preferential physical solvent to produce a hydrogen-rich overhead stream and a rich solvent bottoms stream; and
B. flashing said bottoms stream to obtain a lean solvent stream for recycling to said contacting step.

26. The process of claim 25, wherein said olefin-containing gas is selected from the group consisting of thermally cracked hydrocarbon gas, catalytically cracked hydrocarbon gas, refinery off-gas, coke-oven gas, and synthesis gas.

27. The process of claim 26, wherein said preferential factor is at least 7.0.

28. The process of claim 25, wherein said preferential physical solvent is selective for ethylene and heavier hydrocarbon components of said $C_2=+$ hydrocarbons such that the relative volatility of methane over ethylene is at least 5.5 and the solubility of ethylene in said solvent is at least 1.0 standard cubic foot of ethylene per gallon of said solvent, or the preferential factor is at least 5.5.

29. The process of claim 28, wherein said flashing additionally produces a stream of $C_1+$ hydrocarbons.

30. The process of claim 29, wherein said stream of $C_1+$ hydrocarbons is contacted with a second lean solvent stream to produce a methane-rich gas stream and a second rich solvent stream from which a product stream of $C_2=+$ hydrocarbons is produced by regeneration thereof.

31. The process of claim 26, wherein said preferential factor is at least 10.0.

32. The process of claim 25, wherein said preferential physical solvent is selected from the group consisting of dialkyl ethers of polyalkylene glycol, N-methyl pyrrolidone, dimethylformamide, propylene carbonate, sulfolane, glycol triacetate, and $C_8$ to $C_{10}$ aromatic compounds having methyl, ethyl, or propyl aliphatic groups specifically consisting a sub-group of o-xylene, m-xylene, p-xylene, hemimellitene, pseudocumene, mesitylene, cumene, o-ethyltoluene, m-ethyltoluene, p-ethyltoluene, n-propylbenzene, isopropylbenzene, indane, durene, isodurene, prehnitene, crude xylenes, toluene transalkylation reaction effluents, extracted $C_9$ naphtha reformates, extracted $C_9$ catalytic reformates, $C_9$ heart cuts of said reformates which are enriched in $C_9$ alkylbenzenes, $C_7$-$C_9$ alkyl aromatics, and mixtures thereof.

33. The process of claim 25 which produces three products, wherein:
A. said countercurrently contacting of said Step A occurs within at least one extraction column to which said olefin-containing gas stream and said stream of lean preferential physical solvent are fed, whereby said gas and said solvent streams pass countercurrently therewithin, to produce at least one overhead stream and at least one bottoms stream; and
B. said regenerating occurs within at least one distillation column to which said at least one bottoms stream is fed to produce at least one overhead product stream and at least one said lean solvent stream.

34. The process of claim 33, wherein:
A. said olefin-containing gas stream is fed to the first of two extraction columns arranged in series, said gas stream passing countercurrently in each said column to a stream of said lean preferential physical solvent, thereby producing a first overhead stream, a first bottoms stream, a second overhead stream, and a second bottoms stream, at least one of said overhead streams being one of said products; and
B. said first and second bottoms streams are fed to two distillation columns which regenerate said streams of said lean preferential physical solvent and produce at least one of said products.

35. The process of claim 34, wherein each said extraction column contains a stripping section, having a heat input means, and an extraction section thereabove.

36. The process of claim 9, wherein said heat input means comprises at least one reboiler.

37. The process of claim 36, wherein at least one said extraction column additionally comprises a rectification section to which a reflux stream is fed, said rectification section being disposed above said extraction section.

38. The process of claim 34, wherein each said lean solvent stream flows as part of a solvent loop, said first extraction column containing a portion of a first solvent loop and said second extraction column containing a portion of a second solvent loop.

39. The process of claim 38, wherein said solvent in said first solvent loop and said solvent in said second solvent loop are the same preferential physical solvent.

40. The process of claim 38, wherein said solvent in said first solvent loop and said solvent in said second solvent loop are different physical solvents.

41. The process of claim 34, wherein:
A. said first overhead from said first extraction column is fed to the second extraction column which produces said hydrogen-rich gas stream as its overhead product stream;
B. said first bottoms stream from said first extraction column is fed to the first of said distillation columns which regenerates the first of said solvent streams and produces said stream of ethylene and heavier hydrocarbons; and
C. said second bottoms stream is fed to the second of said distillation columns which produces a methane-rich product stream as its overhead stream.

42. The process of claim 34, wherein:
A. said first overhead stream is said hydrogen-rich product stream;
B. said first bottoms stream is fed to the first of said distillation columns which regenerates the first stream of said lean prefernetial physical solvent and produces an overhead stream of methane and heavier hydrocarbons which is fed to said second extraction column;
C. said second extraction column produces a methane-rich stream as one of said overhead product streams and said second bottoms stream; and
D. said second bottoms stream is fed to said second distillation column which regenerates the second stream of said preferential physical solvent and produces said product stream of ethylene and heavier hydrocarbons.

43. The process of claim 33, wherein said overhead stream is fed to a second extraction column to which said regenerated stream of lean preferential physical solvent is fed, producing said hydrogen-rich stream, as a second overhead stream, and a second bottoms stream which is reduced in pressure ot produce a methane-rich product stream and a second stream of said preferential physical solvent which is fed to a first extraction column.

44. The process of claim 43, wherein said first overhead stream is passed through and compressed within a power recovery turbine through which said second overhead stream is also passed for power recovery.

45. A process for treating a feed stream of gases containing hydrogen, methane, and $C_2=+$ hydrocarbons which has been compressed, cooled, sweetened, and dehydrated, comprising the following steps:
A. contacting said feed stream with a stream of a lean preferential physical solvent to produce a hydrogen-rich overhead product stream and a rich solvent bottoms stream;
B. regenerating said bottoms stream to produce said lean solvent stream for recycling to said contacting step and to produce a second overhead stream of methane and said $C_2=+$ hydrocarbons;
C. contacting said second overhead stream with a second lean solvent stream to produce a methane-rich overhead product stream and a second rich solvent bottoms stream; and
D. regenerating said second bottoms stream to produce a second overhead product stream comprising said $C_2=+$ hydrocarbons and to produce a second lean solvent stream for recycling to said contacting of said Step C.

46. The process of claim 45, wherein said olefin-containing gas is seleclted form the group consisting of thermally cracked hydrocarbon gas, catalytically cracked hydrocarbon gas, refinery off-gas, coke-oven gas, and synthesis gas.

47. The process of claim 46, wherein said preferential physical solvent is selective for ethylene and heavier hydrocarbon components of said $C_2=+$ hydrocarbons such that the relative volatility of methane over ethylene is at least 5.5 and the solubility of ethane in said solvent is at least 1.0 standard cubic foot of ethylene per gallon of said solvent, or the preferential factor is at least 5.5.

48. The process of claim 45, wherein said prefernetial physical solvent is selected from the group consisting of dialkyl ethers of polyalkylene glycol, N-methyl pyrrolidone, dimethylformamide, propylene carbonate, sulfolane, glycol triacetate, and $C_8$ to $C_{10}$ aromatic compounds having methyl, ethyl, or propyl aliphatic groups specifically consisting a sub-group of o-xylene, m-xylene, p-xylene, hemimellitene, pseudocumene, mesitylene, cumene, o-ethyltoluene, m-ethyltoluene, p-ethyltoluene, n-propylbenzene, isopropylbenzene, indane, durene, isodurene, prehnitene, crude xylenes, toluene transalkylation reaction effluents, exracted $C_9$ naphta reformates, extracted $C_9$ catalytic reformates, $C_9$ heart cuts of said reformates which are enriched in $C_9$ alkylbenzenes, $C_7$–$C_9$ alkyl aromatics, and mixtures thereof.

49. The process of claim 45, wherein said solvent has a preferential factor of 7.0 and ethylene is capable or recovery from said gas stream at up to at least 80% recovery and and is capable of purification up to ethylene product specification levels of methane.

50. A process for producing an $H_2$-rich gas product stream from an inlet hydrocarbon gas stream containing hydrogen and $C_1$ and $C_2=+$ hydrocarbons, comprising the following steps:
A. countercurrently contacting said gas steam with a stream of a lean preferential physical solvent, which is selective for ethylene and heavier hydrocarbon components of said hydrocarbon gas stream such that the relative volatility of methane over ethylene is at least 5.5 and the solubility of ethylene in said solvent is at least 1.0 standard cubic foot of ethylene per gallon of said solvent, or the preferential factor is at least 5.5, to produce said $H_2$-rich gas product stream as a first overhead stream and a rich solvent stream containing said $C_2=+$ hydrocarbons as a first bottoms stream; and
B. distilling said rich solvent stream to produce said lean solvent stream as a second bottoms stream and a mixture of said $C_1$ and said $C_2=+$ hydrocarbons as a second overhead stream containing up to 99.5% of the ethylene in said inlet gas stream.

51. The process of claim 50, wherein said solvent is selected form the group consisting of dialkyl ethers of polyalkylene glycol, N-methyl pyrrolidone, dimethylformamide, propylene carbonate, sulfolane, glycol triacetate, and $C_8$ to $C_{10}$ aromatic compounds having methyl, ethyl, propyl aliphatic groups specifically constituting a sub-group of o-xylene, m-xylene, p-xylene, hemimellitene, pseudocumene, mesitylene, cumene, o-ethyltoluene, m-ethyltoluene, p-ethyltoluene, n-propylbenzene, isopropylbenzene, indane, durene, isodurene, prehnitene, crude xylenes, toluene transalkylation reaction effluents, extracted $C_9$ naphtha reformates, extracted $C_9$ catalytic reformates, $C_9$ heart cuts of said reformates which are enriched in $C_9$ alkybenzenes, $C_7$–$C_9$ alkyl aromatics, and mixtures thereof.

52. The process of claim 50, wherein said hydrcarbons principally comprise methane.

53. The process of claim 50, wherein said inlet gas stream is selected from the group consisting of thermally cracked hydrocarbon gas, catalytically cracked hydrocarbon gas, refinery off-gas, coke-oven gas, and synthesis gas.

54. A process for separating the components of a compressed, sweetened, and dehydrated hydrocarbon gas stream containing hydrogen, methane, and olefins, comprising the following steps:

A. selectively contacting said gas stream with a stream of a preferential physical solvent, having a preferential factor of at least 7.0, to produce an overhead gas stream of said methane and said hydrogen and a rich solvent bottoms stream; and B. regenerating said solvent from said bottoms stream for recycling to said contacting step and to produce an overhead stream of said olefins from which 99% of the ethylene is recoverable at a purity of up to 99.5%.

55. The process of claim 54, wherein said regenerating is carried out by flashing and/or distilling.

56. The process of claim 54, wherein said preferential physical solvent is selected from the group consisting of dialkyl ethers of polyalkylene glycol, N-methyl pyrrolidone, dimethylformamide, propylene carbonate, sulfolane, glycol triacetate, and $C_8$ and $C_{10}$ atomatic compounds having methyl, ethyl, or propyl aliphatic groups specifically constituting a sub-group of o-xylene, m-xylene, p-xylene, hemimellitene, pseudocumene, mesitylene, cumene, o-ethyltoluene, m-ethyltoluene, p-ethyltoluene, n-propylbenzene, isopropylbenzene, indane, durene, isodurene, prehnitene, crude xylenes, toluene transalkylation reaction effluents, extracted $C_9$ naphtha reforamtes, extracted $C_9$ catalytic reformates, $C_9$ heart cuts of said reformates which are enriched in $C_9$ alkybenzenes, $C_7$–$C_9$ alkyl aromatics, and mixtures thereof.

57. The process of claim 54, wherein said olefin-containing gas is selected from the group consisting of thermally cracked hydrocarbon gas, catalytically cracked hydrocarbon gas, refinery off-gas, coke-oven gas, and synthesis gas.

* * * * *

UNITED STATES PATENT AND TRADEMARK OFFICE
CERTIFICATE OF CORRECTION

PATENT NO. : 4,743,282
DATED : May 10, 1988
INVENTOR(S) : Yuv R. Mehra

It is certified that error appears in the above-identified patent and that said Letters Patent is hereby corrected as shown below:

Claim 4, col. 25, line 39, change "$C_8$ and $C_{10}$" to --$C_8$ to $C_{10}$--.

Claim 56, col. 32, line 9, change "$C_8$ and $C_{10}$ atomatic" to --$C_8$ to $C_{10}$ aromatic--.

Signed and Sealed this

Twenty-seventh Day of September, 1988

Attest:

DONALD J. QUIGG

*Attesting Officer*     *Commissioner of Patents and Trademarks*